United States Patent [19]
Corrigan et al.

[11] Patent Number: 5,585,575
[45] Date of Patent: Dec. 17, 1996

[54] EXPLOSIVE DETECTION SCREENING SYSTEM

[75] Inventors: Colin Corrigan; Lawrence Haley, both of Ottawa, Canada

[73] Assignee: Research Corporation Technologies, Inc., Tucson, Ariz.

[21] Appl. No.: 468,866

[22] Filed: Jun. 6, 1995

Related U.S. Application Data

[62] Division of Ser. No. 224,230, Apr. 7, 1994, which is a division of Ser. No. 859,509, Aug. 6, 1992, Pat. No. 5,345,809, which is a continuation-in-part of Ser. No. 447,724, Dec. 8, 1989, Pat. No. 4,987,767, which is a continuation-in-part of Ser. No. 364,663, Jun. 9, 1989, abandoned.

[51] Int. Cl.$^6$ .................. G01N 1/22; G01N 33/22
[52] U.S. Cl. .................. 73/863.71; 73/863.21; 73/864.33; 73/23.2; 73/23.33
[58] Field of Search .................. 73/863.73, 863.71, 73/863.23, 863.21, 23.2, 863.12, 21.08, 23.31, 31.07, 23.33, 864.33

[56] References Cited

U.S. PATENT DOCUMENTS

| | | | |
|---|---|---|---|
| 4,111,049 | 9/1978 | Lerner | 73/421.5 R |
| 4,117,714 | 10/1978 | Goodson et al. | 73/23 |
| 4,586,367 | 5/1986 | Lewis | 73/23 |
| 4,718,268 | 1/1988 | Reid et al. | 73/23 |
| 4,754,655 | 7/1988 | Parker, III et al. | 73/864.44 |
| 4,786,472 | 11/1988 | McConnell et al. | 422/61 |
| 4,820,920 | 4/1989 | Bather | 250/282 |
| 4,821,737 | 4/1989 | Nelson | 128/730 |
| 4,961,916 | 10/1990 | Lesage et al. | 422/88 |
| 4,964,309 | 10/1990 | Jenkins | 73/864.81 |
| 4,987,767 | 1/1991 | Corrigan et al. | 73/23.36 |
| 5,025,653 | 6/1991 | Schuldt | 73/1 G |
| 5,138,889 | 8/1992 | Conrad | 73/863.12 |
| 5,162,652 | 11/1992 | Cohen et al. | 250/288 |

FOREIGN PATENT DOCUMENTS

| | | | |
|---|---|---|---|
| 0458622 | 11/1991 | European Pat. Off. | 73/864.33 |

Primary Examiner—Hezron E. Williams
Assistant Examiner—J. David Wiggins
Attorney, Agent, or Firm—Scully, Scott, Murphy & Presser

[57] ABSTRACT

An explosive detection screening system used for the detection of explosives and other controlled substances such as drugs or narcotics. The screening system detects the vapor and/or particulate emissions from the aforementioned substances and reports that they are present on an individual or object and the concentration of each substance detected. The screening system comprises a sampling chamber for the collection of the vapor and/or particulate emissions, a concentration and analyzing system for the purification of the collected vapor and/or particulate emissions and subsequent detailed chemical analysis of the emissions, and a control and data processing system for the control of the overall system.

44 Claims, 17 Drawing Sheets

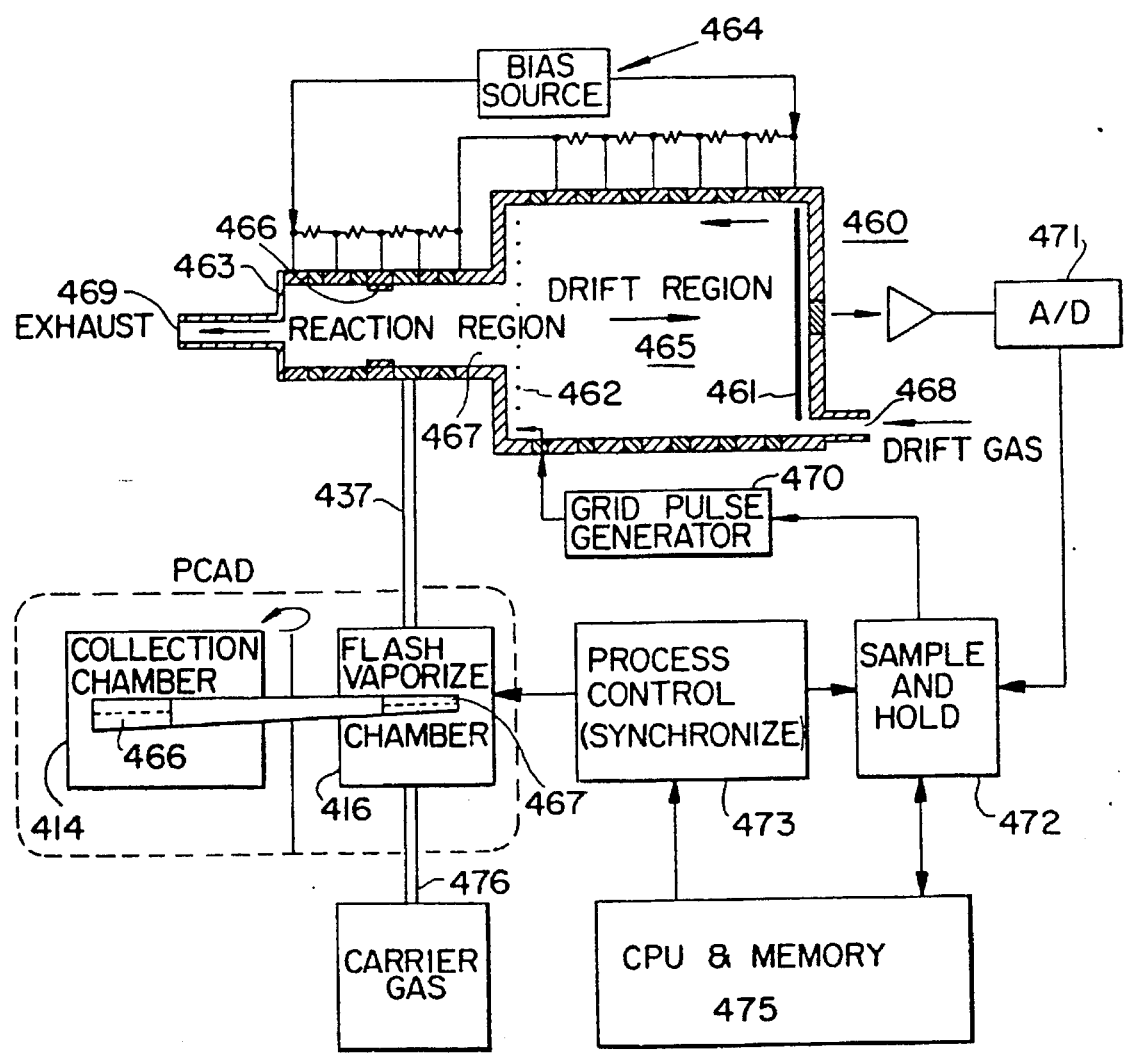

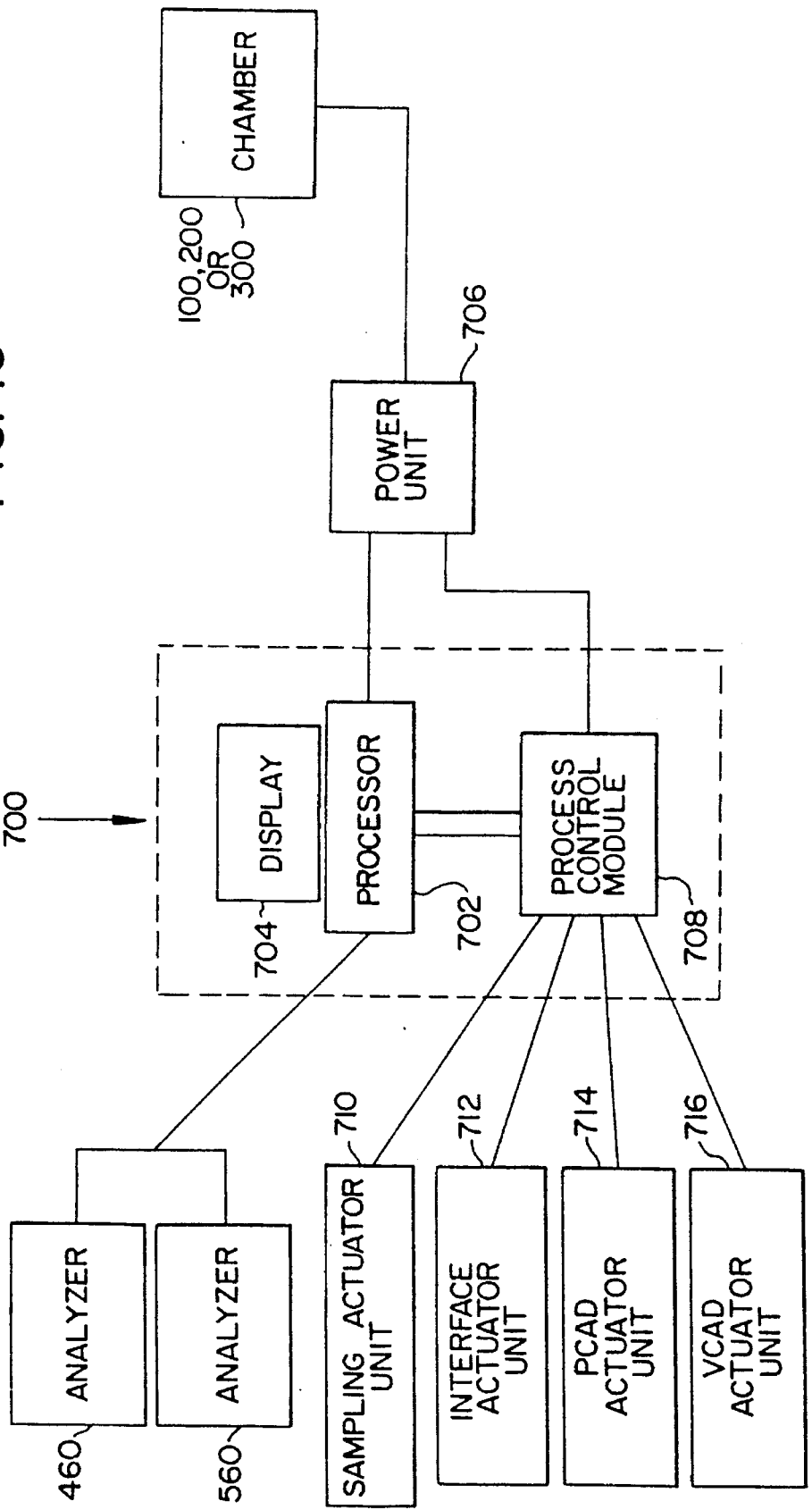

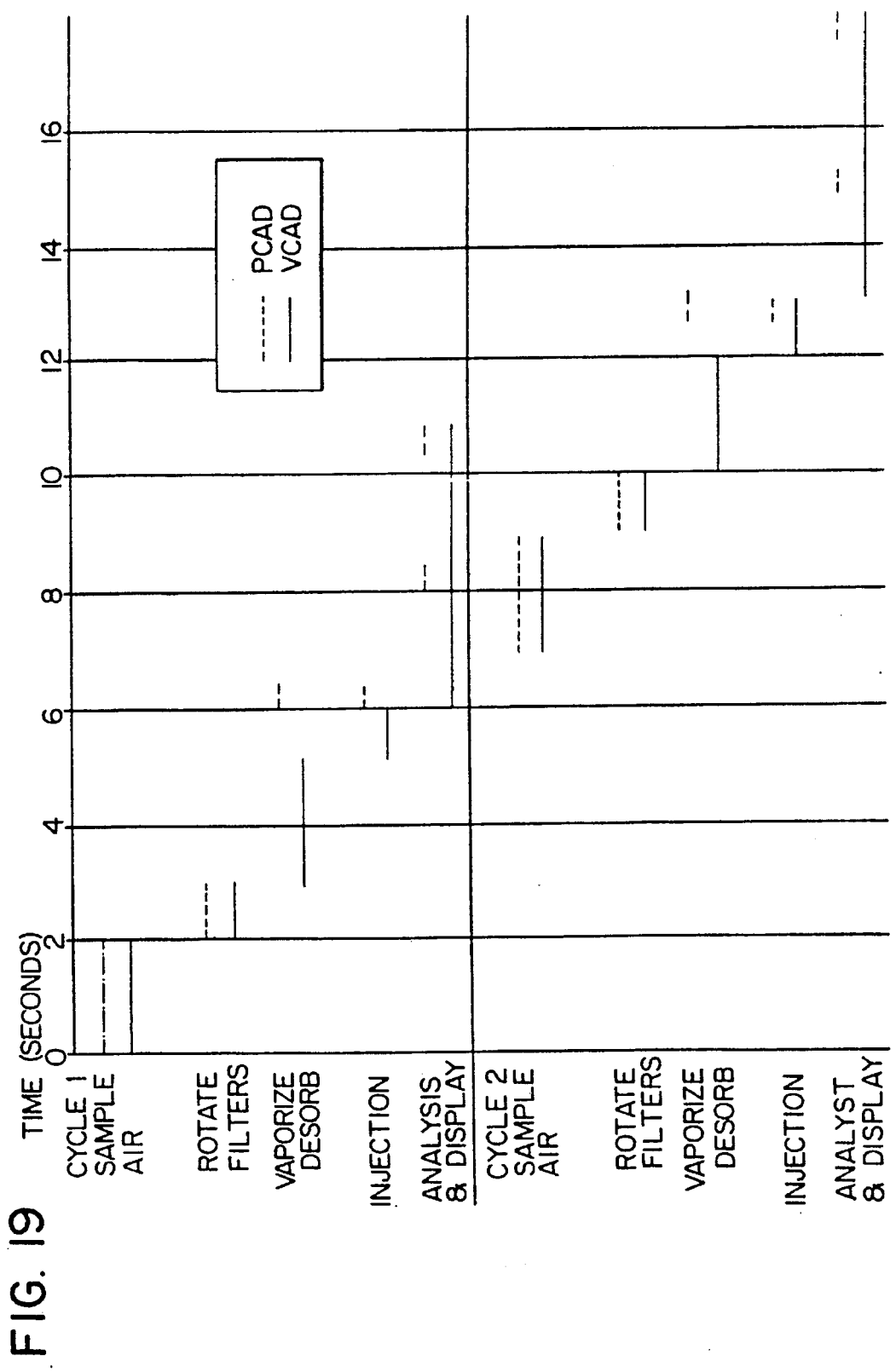

EXPLOSIVE DETECTION SCREENING SYSTEM

This is a divisional of application Ser. No. 08/224,230, filed on Apr. 7, 1994, which is a divisional application of U.S. Ser. No. 859,509 filed Aug. 6, 1992 from a PCT Dec. 10, 1990, now U.S. Pat. No. 5,345,809, which is a continuation-in-part application of U.S. Ser. No. 447,724 filed Dec. 8, 1989, now U.S. Pat. No. 4,987,767, which is a continuation-in-part application of U.S. Ser. No. 364,663, filed Jun. 9, 1989, now abandoned.

BACKGROUND OF THE INVENTION

1. Field of the Invention

This invention relates to systems for the detection of explosives and other controlled substances such as drugs or narcotics. More particularly, the present invention relates to an integrated system consisting of a sampling chamber, a detection system, and a control and data processing system, for the detection of the vapor emissions and particulates associated with explosives and controlled substances in a non-invasive manner.

2. Discussion of the Prior Art

In recent years there has been a steady increase in the illegal use of explosives as well as an increase in the transportation of contraband substances such as drugs or narcotics. It is impossible to detect the existence or prevent all of the cases of bombings and drug smuggling going on; however, it is possible to detect explosives and contraband substances in particular areas where high visibility and/or vulnerability exists such as in airports or airplanes. There are numerous ways in which an individual can place drugs or explosives on an airplane, and even more places an individual can hide the drugs or explosives once on the airplane. The illegal substances can be brought on the airplane by a knowing or unknowing individual by concealing the substance on his/her person or by placing the substances in baggage to be placed in the cargo section of the aircraft.

The methods for detecting substances such as explosives and drugs or narcotics have been studied for many years, and various techniques have been developed which range from explosives/drug sniffing dogs to highly sophisticated vapor detection devices. Basically, the detection of the aforementioned substances is accomplished in one of two ways; namely, non-vapor detection and vapor detection. Non-vapor detection methods include x-ray detection, gamma-ray detection, neutron activation detection and nuclear magnetic resonance detection. These methods of detection are more applicable to the detection of the various substances when the substances are concealed and are carried or associated with non-living items such as baggage to be carried onto an aircraft in that the detection techniques might pose a threat to living items. Vapor detection methods include electron capture detection, gas chromatography detection, mass spectroscopy detection, plasma chromatography detection, bio-sensor detection and laser photoacoustic detection. These methods of detection are more applicable to the detection of substances that are concealed and associated with living items such as those that can be carried by individuals including the residuals left on the individual who handled the various substances. All of the above methods are presently utilized, including explosive and drug sniffing dogs.

Today, there are many private and government research studies devoted to the development of systems and methods for the detection of explosives and drugs or narcotics. With the advances in explosives technology, such as the advent of the plastique explosives, which can be disguised as common items, it is becoming increasingly difficult to detect these substances. The problems that must be overcome in the detection of these substances as well as others, include low vapor pressure of the particular vapors escaping from the particular substance, the search time and the throughput of the various systems, the low concentration of vapor or particulate emissions from the particular substance, isolation of the particular substance with a high degree of reliability, and maintaining the integrity of the systems environment.

There is substantial prior art dealing with the technology of explosive and drug detection devices. The article "Air Flow Studies For Personnel Explosive Screening Portals" authored by R. L. Schellenbaum of Sandia National Laboratories, which was published in 1987 as part of the Carnahan Conference on Securities Technology in Atlanta, Ga. (Jul. 15, 1987), discloses a study on various types of integrated systems for the detection of contraband explosives. The study outlined a three step process, which includes the collection of vapor, preconcentration, and detection of the vapors emanating from explosive substances. The article discloses various types of collection devices for collecting the sample. Various portal configurations and air flow mechanics within each of the portals were studied to see which one provided the best sample. The Atmos-Tech Air Shower Portal, a Modified Atmos-Tech Portal and a Cylindrical Portal were used in the study with various air flow configurations. The study concluded that downward, semi-laminar flow over the body cross-sectional area combined with a vacuum flow collection funnel of approximately twelve inches in diameter placed beneath the grating in the floor of the portal was the best way to collect the explosives vapor or particulate emissions from an individual passing through the portal.

For the detection part of the study, various detection devices were used including the Phemto-Chem 100 Ion Mobility Spectrometer in combination with a preconcentrator developed by Ion Track Instruments Inc. The ion mobility spectrometer is a plasma chromatograph which uses an atmospheric ion-molecule reactor that produces charged molecules which can be analyzed by ion mobility. The preconcentrator comprises a motor-driven, coated metal screen disc rotated with a cast metal casing. The coating on the screen adsorbs the vapor and is then heated for desorption of the vapor. This adsorption-desorption process is a necessary preconcentration step which is used to increase the vapor and/or particulate concentration in the collected air sample.

The major problem encountered in the use of the portal detection systems in the study was maintaining the integrity of the sample air volume. In maintaining the integrity of the sample air volume, it is necessary to prevent the sample air volume from being contaminated with the ambient environment at the same time trying to maintain a steady flow of traffic through the portal, which is essential to efficient operation of any type of screening system in which heavy traffic is common place. The aforementioned article suggests that the integrity of the sample air volume was not maintained in portals without doors. If ambient drafts were present, such as those from air conditioners or just the flow of pedestrian traffic, a reduction of ten percent in detection was encountered. The addition of doors on the portals effected a rise in the detection rate; however, it produced unacceptable pedestrian traffic problems which would not meet the requirements for high throughputs required by airports.

In the patent art, there are a group of references which disclose various methods and devices for detecting contraband substances, including both drugs and explosives. These references are all directed to the detection of contraband substances within a container or luggage, and not those carried on a person. U.S. Pat. No. 4,580,440 and U.S. Pat. No. 4,718,268 both assigned to British Aerospace Public Company Limited disclose a method and apparatus for detecting contraband substances sealed in freight type cargo. Basically, the method consists of sealing the cargo in a container, agitating the cargo in order to shake off the vapor or particulate matter emanating from the cargo into the surrounding atmosphere, sampling the atmosphere, heating the collected sample and analyzing the sample utilizing gas chromatography. U.S. Pat. No. 4,202,200 assigned to Pye Limited discloses an apparatus for detecting explosive substances in closed containers. Basically, objects such as luggage are passed through a controlled axis tunnel wherein the objects are swept by circulating air flows, and then the air sample is collected and analyzed. It is also suggested that if a larger tunnel is constructed, people as well as objects can be passed through it. The aforementioned inventions provide a means and method for detecting contraband substances by using vapor sampling; however, none of the inventions provide or suggest the use of a preconcentrator means for increasing the sensitivity and selectivity of the detection means. Additional patent references which disclose similar type systems are U.S. Pat. No. 3,998,101 and U.S. Pat. No. 4,111,049.

There are numerous patent references in the testing and monitoring art which disclose a concentration step which includes the filtration or absorption of the molecules of interest over time. After a predetermined period of exposure, the filtering/absorption media is removed and desorbed with heat, while a new filter/absorption media is placed in the air stream. U.S. Pat. No. 3,768,302 assigned to Barringer Research Limited discloses a system used in the geological testing area and in which the system receives an air stream containing particulates. The sample undergoes a concentration step which includes passing the air sample over two paths with adsorbing/desorbing steps, before finally being analyzed. U.S. Pat. No. 4,056,968 assigned to the same assignee as the above patent also discloses a system which is also used in the geological testing area. In this invention, the concentrated molecules could be desorbed from a moving tape as well as from a moving disk. U.S. Pat. No. 4,775,484 discloses a rotating filter media which is used to absorb particulate material during one stage of its rotation, and which is purged or cleaned at a separate and second stage of its rotation. U.S. Pat. No. 4,127,395 also discloses a common absorption/desorption circuit using a pair of absorbent media, wherein one of the pair is absorbing, while the other is desorbing. U.S. Pat. No. 3,925,022, U.S. Pat. No. 3,997,297 and U.S. Pat. No. 3,410,663 all disclose absorption/desorption type devices. All of the aforementioned devices disclose systems for the absorption and subsequent desorption of particulate or vapor matter; however, none disclose a portal type sampling chamber.

SUMMARY OF THE INVENTION

The present invention is directed to a system for the detection of explosives, chemical agents and other controlled substances such as drugs or narcotics by detecting their vapor emissions or the particulates associated with these materials. The system comprises a sampling means, first and second sample collection and analysis subsystems, and a control and data processing system. The system is particularly useful in field environments, such as airports, where it can be used to detect the aforementioned substances on an individual or in the baggage of the individual. The system meets the requirement to detect the aforementioned substances in a non-invasive manner at any required level, and to do it so quickly that the free passage of people and baggage is not unduly interrupted.

The sampling means takes on a variety of forms including a sampling chamber portal; a hand-held wand, and an automated baggage/parcel sampling chamber. The sampling chamber portal is a portal with internal dimensions of approximately six feet in length, seven feet in height and three feet in width. The dimensions of the portal are such as to allow an average sized individual as well as a wheel chair bound individual to easily pass through. The portal is designed in such a way as to have an internal air flow sweep over an individual walking or passing through the portal at a normal walking pace, and at the same time have the air sample swept from the individual contain a meaningful concentration of vapors or particulate matter to be analyzed. To accomplish this, the sampling chamber or portal is designed with a unique geometry and contains air guides or jets for providing an air flow which effectively isolates the internal air volume from the ambient environment while efficiently sweeping the individual passing through the portal. The air volume or sample inside the portal is collected through a sampling port located within the ceiling section of the portal. The air sample is then transported to the first and second sample collection and analysis subsystems for analysis.

The hand-held wand is a sampling means for gathering a sample volume of air from a specific area on an individual or object and for removing particulate matter from the individual or object and introducing the particulate matter into a sample volume of air for analysis while preventing contamination of the sample with the ambient environment. The hand-held wand includes a rotating brush located at the inlet part of the wand. The rotating brush effectively sweeps any particulate matter attached to the individual or object into a vacuum flow created by a vacuum fan in the main system. The hand-held wand is uniquely designed such that it may form a substantially air tight seal with an individual or object, such as a piece of luggage. The sample volume of air containing vapors and/or particulates is then transported to the first and second sample collection and analysis subsystems for analysis.

The automated baggage/parcel sampling chamber is a sampling means for gathering a sample volume of air surrounding an object, such as luggage, and for removing particulate matter from all exposed surfaces of the object and introducing the particulate matter into the sample volume of air. The automated baggage/parcel sampling chamber is of a rectangular open ended tunnel form. Typically, the size of the automated baggage/parcel sampling chamber would be approximately the size of the baggage scanning x-ray devices currently utilized in airports. It is fitted over a conveyer belt which is used to carry the baggage parcels through the tunnel. The automated baggage/parcel sampling chamber is fitted with at least four sampling heads which brush over-all exposed surfaces of the object. These sampling heads contain rotating brushes that sweep the exposed surfaces and introduce the particulates and any vapor emanating from the object into a sample volume of air. The sample volume of air containing vapors and/or particulates is then transported to the first and second sample collection and analysis subsystems for analysis.

The plurality of sampling means are capable of collecting and delivering to the first and second sample collection and analysis subsystems vapor and/or particulate matter when they are present in as low a concentration as several parts per trillion of ambient air.

The first and second sample collection and analysis subsystems are devices which are used to collect vapors emanating from and particulates associated with the particular class of materials discussed above. The first sample collection and analysis subsystem is a sample collector and vaporizer which converts collected particulates into a first vapor sample for analysis. This first vapor sample for analysis is delivered to a fast response chemical analyzer which may be either a gas chromatograph/electron capture detector or an ion mobility spectrometer or both. The basic principle of operation is the collection of particulate matter on a filter element and the use of flash heating to vaporize the collected matter. The second sample collection and analysis subsystem is a vapor collector and detector which through a series of steps of decreasing sample volume and increasing sample concentration, delivers a concentrated sample to a fast response chemical analyzer which may be either a gas chromatograph/electron capture detector or an ion mobility spectrometer or both. The principle of operation is one of adsorbing the sample onto a selected substrate with subsequent selective thermal desorption to create a second vapor sample for analysis. This process is repeated through a series of steps of decreasing sample volume and increasing sample concentration. Upon completion of the preconcentration steps, the purified sample material is analyzed by the aforementioned devices wherein the analysis consists of identifying the various materials and determining the amount of material present.

The total system and all system processes are controlled by the control and data processing system which comprises a digital computer and associated software. The system is configured and controlled to make all required measurements and prepare the results in a usable and intelligible format. The control and data processing system controls the collection of the vapors and particulates, the vaporization of collected particulates, the preconcentration of collected vapors, the various chemical analysis steps, and the data analysis and data formatting. In addition, the computer continuously performs self diagnostic and self calibration procedures on the total system and alerts the user to any potential problems.

The system for the detection of explosives and other controlled materials of the present invention provides for the efficient detection of explosives, chemical agents or other controlled materials such as drugs or narcotics by detecting the vapor emissions and particulates associated with these substances. The vapor emissions and particulates can come from substances concealed on the individual, the individual's baggage, or from a residue left on an individual who handled the particular substance. The present invention provides a system with a high degree of sensitivity and selectivity to a wide range of substances. The high degree of sensitivity and selectivity is accomplished by employing a system which utilizes the combination of unique sampling means and a multi-stage preconcentrator and vaporizer that decreases sample volume while maximizing sample concentration thereby allowing much larger sample volumes to be taken as well as much shorter sample collection times. The system provides a high reliability rate which is accomplished by utilizing the computer control and data processing system for automatic calibration and self diagnostic procedures. In addition, the system provides a nigh degree of versatility in that by changing the programming of the computer, a wide range of explosives, controlled chemical agents, and drugs and narcotics which have differing physical and chemical properties can be detected. Having the total system under software control provides a more versatile system and one that is easily reconfigurable.

The present invention has a wide variety of applications where a high throughput of people is required. In airports, the detection of explosives and controlled substances is of paramount importance due to the rise in terrorist attacks and drug smuggling. The present invention allows for the fast and reliable detection of the aforementioned substances in a non-invasive manner in a variety of field environments such as in airports. The system of the present invention is applicable where the detection of concealed substances is absolutely required.

BRIEF DESCRIPTION OF THE DRAWINGS

For the purpose of illustrating the invention, there is shown the drawings the forms which are presently preferred; however, it should be understood that the invention is not necessarily limited to the precise arrangements and instrumentalities here shown.

FIG. 11D is a diagrammatic illustration of the chemical analyzer utilized by the first sample collection and analysis subsystem of the present invention;

FIG. 16 is a block diagram of the control and data processing system of the present invention;

FIG. 19 is a timing chart illustrating the various time parameters for the various processes of the present invention.

DESCRIPTION OF THE PREFERRED EMBODIMENT

Figure 1A:
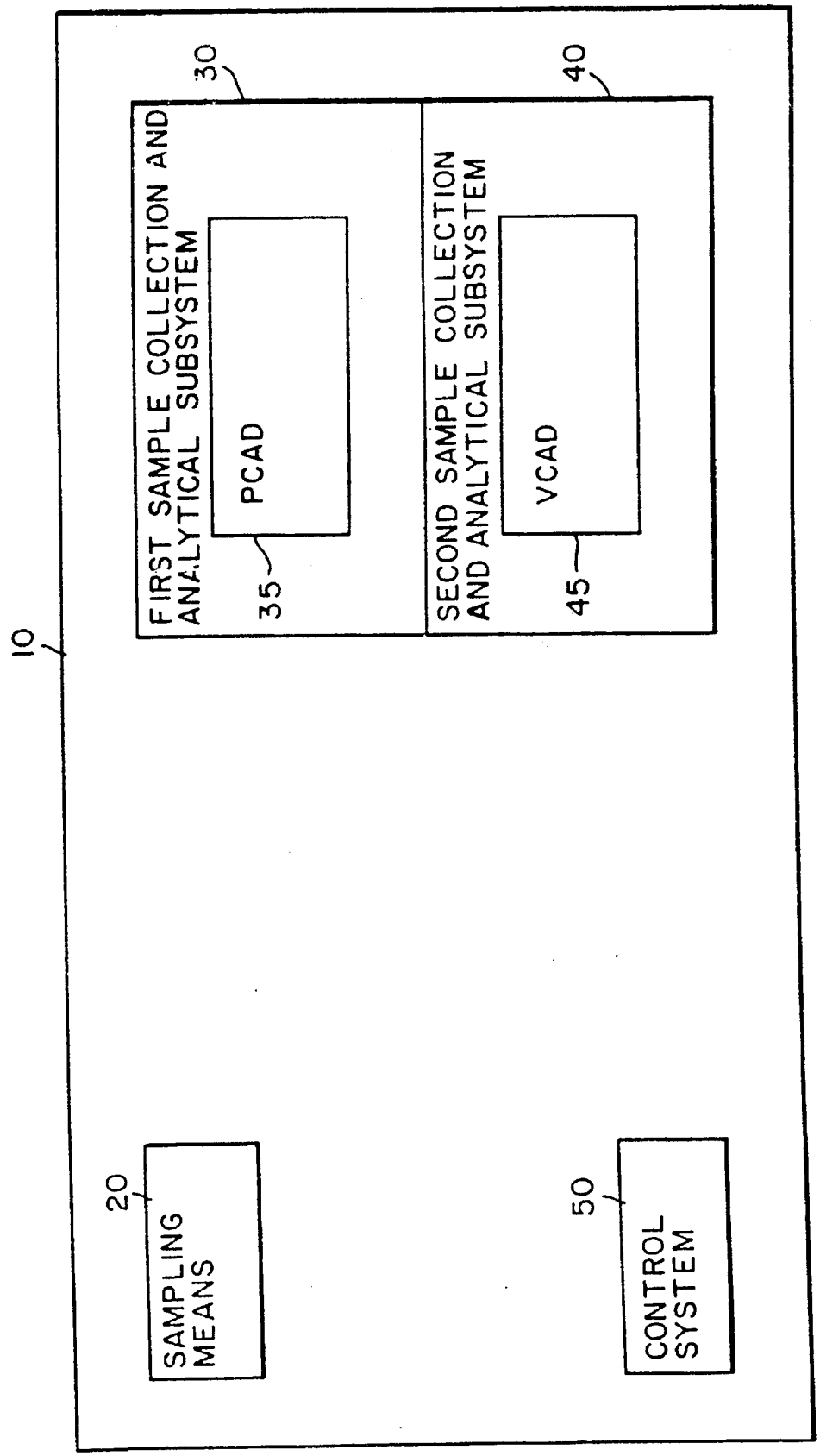
FIG. 1A is a high level block diagram of the explosive detection screening system of the present invention.

The explosive detection screening system of the present invention is designed to detect explosives, chemical agents or other controlled materials such as drugs or narcotics by detecting vapors emanating from or particulates associated with each of these materials. These substances are assumed to be concealed on individuals or in their baggage in airports or in other high vulnerability, high visibility environments. It is necessary to detect these substances in a non-invasive manner at any required level, and to do it so quickly that the free passage of people and baggage is not unduly interrupted. The system is an integrated system comprising a sampling means, a first and second sample collection and analysis subsystem and a control and data processing system.

In a first embodiment, the sampling means is a sampling chamber portal in which internally generated air flows sweep the vapor emissions emanating from or particulates associated with an individual or object passing through the chamber to a collection area. This portal is more fully described in the parent applications U.S. Ser. No. 364,663, filed Jun. 9, 1989, and U.S. Ser. No. 447,724, filed Dec. 8, 1989. The sampling chamber portal is designed in such a way as to capture a high enough concentration of vapor emissions and/or particulates so as to be able to detect the presence of the aforementioned substances with a high degree of reliability and dependability. The internal volume of air is recirculated with a small amount being removed at the sampling time. At the sampling time, or more commonly referred to as the sampling period, an external air pump or fan draws a sample of the collected air volume into the first and second sample collection and analysis subsystems.

In a second embodiment, the sampling means is a hand-held wand. The hand-held wand is a sampling means for gathering a sample volume of air from a specific area on an individual or object and for removing particulate matter from the individual or object and introducing the particulate matter into the sample volume of air for analysis while preventing contamination of the sample with the ambient environment. The hand-held wand consists of a rotating brush located at the inlet port of the wand. The rotating brush effectively sweeps any particulate matter attached to the individual or object into an air flow created by a vacuum fan in the base system. The hand-held wand is uniquely designed such that it forms a substantially air tight seal with the individual or object. The sample volume of air containing vapors and/or particulates is then transported to the first and second sample collection and analysis subsystems.

In a third embodiment, the sampling means is an automated baggage/parcel sampling chamber. The automated baggage/parcel sampling chamber is a sampling means for gathering a sample volume of air surrounding an object and for removing particulate matter from all exposed surfaces of the object and introducing the particulate matter into the sample volume of air. The automated baggage/parcel sampling chamber is of a rectangular open ended tunnel form. Typically, the size of the automated baggage/parcel sampling chamber would be approximately the size of the baggage scanning x-ray devices currently utilized in airports. It is fitted over a conveyer belt which is used to carry the baggage or parcels through the tunnel. The automated baggage/parcel sampling chamber is fitted with at least four sampling heads which brush over all surfaces of the object. These sampling heads contain rotating brushes that sweep the exposed surfaces and introduce the particulates and any vapor emanating from the object into the sample volume of air. The sample volume of air containing vapors and/or particulates is then transported to the first and second sample collection and analysis subsystems.

The plurality of sampling means are capable of collecting and delivering to the first and second sample collection and analysis subsystems vapor and/or particulate matter when they are present in as low a concentration as several parts per trillion of ambient air in a short period of time.

The first and second sample collection and analysis subsystems are devices which are used to collect vapors emanating from and particulates associated with the particular class of materials discussed above. The first sample collection and analytical subsystem in a sample collector and vaporizer which converts collected particulates into a first vapor sample for analysis. This first vapor sample for analysis is delivered to a fast response chemical analyzer which may be either a gas chromatograph/electron capture detector or an ion mobility spectrometer or both. In the preferred embodiment, an ion mobility spectrometer is utilized as the chemical analyzer. The second sample collection and analysis subsystem is a vapor collector and detector which through a series of steps of decreasing sample volume and increasingly sample concentration, delivers a concentrated sample to a fast response chemical analyzer which may be either a gas chromatograph/electron capture detector or an ion mobility spectrometer or both. In the preferred embodiment, a gas chromatograph/electron capture detector is used as the chemical analyzer. The principle of operation is one of adsorbing the sample onto a selected substrate with subsequent selective thermal desorption. This process is repeated through a series of steps of decreasing sample volume and increasing sample concentration. Upon completion of the preconcentration steps, the purified sample material is analyzed by the aforementioned devices wherein the analysis consists of identifying the various materials and determining the amount of material present.

The control system is a control and data processing system of which the primary requirement is to report the presence of, and if required, the level of a specified substance. The system may also be capable of distinguishing between background levels of a substance and alarm levels. The system also controls the operation of the entire system by automatic control methods which is run by a microprocessor or digital computer. The control system is easily reprogrammed to detect various substances because of modularized programming techniques.

Referring to FIG. 1A, there is shown a block diagram of the explosive detection screening system 10 of the present invention. As is shown in the Figure, the explosive detection screening system comprises a sampling means 20, a first sample collection and analysis subsystem 30 which comprises a particulate collector and detector 35, a second sample collection and analysis subsystem 40 which comprises a vapor collector and detector 45, and a control and data processing system 50 which controls all phases of system operation.

The particulate collector and detector 35, PCAD, comprises a sample collector and vaporizer, SCAV, and a chemical analyzer which may be either a gas chromatograph/election capture detector or an ion mobility spectrometer or both. The primary function of the PCAD 35 is to collect and analyze particulates in the sample volume of air collected by the sampling means for the chemical compounds of interest. The primary function is accomplished by first collecting and converting the particulates to vapor in the SCAV and then submitting the vapors to the chemical analyzer for analysis.

In the collection of particulate matter and the subsequent vaporization of the particulate matter, there are various problems that are encountered and which must be solved. The first problem encountered is the collection of the particulates of interest. The particulates of the various compounds are varied in size and thus different size collection elements must be utilized. In addition, the particulates may be attached to larger particles such as water vapor or dust. Since it is possible for many types of particulates to be contained in a specific volume of air, the collection element must be such that it selectively adsorbs only particulates of interest. The present invention utilizes varying size filter mesh elements, or a plurality of adsorbent materials adjacent or on the filter elements to adsorb the various particulates. The second problem encountered is that the particulate matter collected must be vaporized. The vaporization process is an extremely important and complicated procedure. Different particulates have different vaporization temperatures and thus the vaporization temperature must be precisely controlled so as to effectively vaporize target particulates, and prevent excessive heat damage to the molecules of interest in the target particulates. The third problem encountered is the problem of concentration. For the best analysis results, the concentration of particulates in a specific volume of air must be as high as possible. Therefore, the vaporization process is combined with the use of a carrier gas, which is utilized to inject the vaporized sample into the chemical analyzer. The solution to these problems as well as others solved by the present invention are more fully discussed in the detailed description of the SCAV.

The vapor collector and detector 45, VCAD, is comprised of a sample collector and preconcentrator, SCAP, and a chemical analyzer which is either a gas chromatograph/ electron capture detector or ion mobility spectrometer or both. The primary function of the VCAD 45 is to collect, preconcentrate and analyze the air sample collected for the target vapors. This function is accomplished by first selectively collecting and preconcentrating the targeted molecules in the SCAP and then submitting the vapors to the chemical analyzer for analysis.

In the collection of vapor matter for analysis, there are two major problems that are encountered. The first problem encountered is that of low concentration of target vapors in the air sample. In any particular sample volume of air collected in the sampling chamber portal, the hand-held wand or in the automated baggage/parcel sampling chamber, the concentration of target vapors is going to be low. Therefore, the SCAP in at least one concentration stage must selectively concentrate the target vapors into a concentrated sample volume while discarding non-target vapors. The second problem encountered is that of heat damage to the molecules in the target vapors. The concentration process involves adsorption and subsequent desorption of the target vapors. This process requires a certain amount of heat to desorb the target vapors from the adsorbent. If too much heat is utilized, the molecules in the target vapors can be destroyed or unduly fragmented and if too little heat is utilized, the target vapors will not be desorbed. The solution to these problems as well as others are discussed in the detailed description of the VCAD.

Figure 1B:
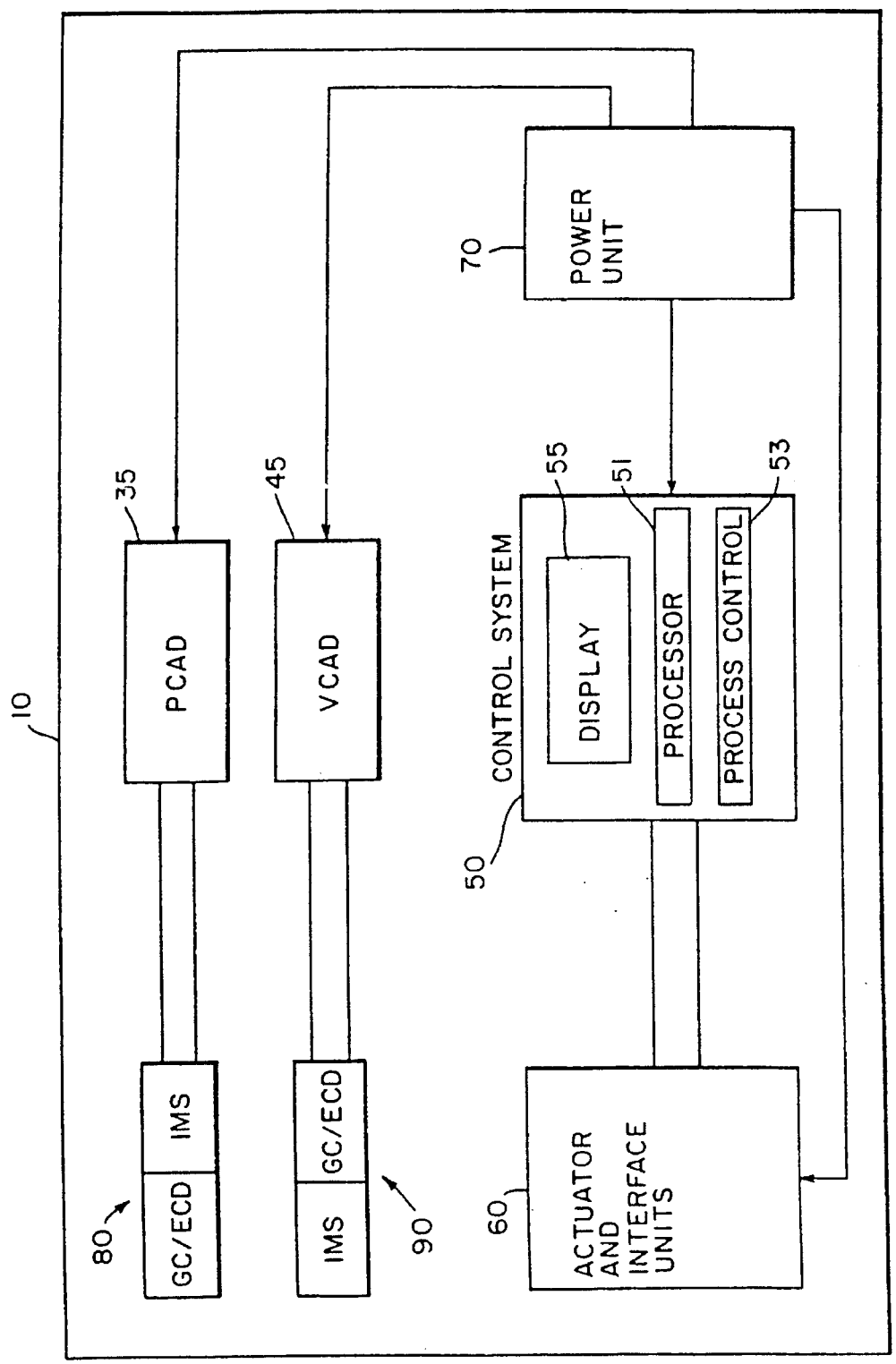
FIG. 1B is a detailed block diagram of the explosive detection screening system of the present invention.

FIG. 1B illustrates a more detailed block diagram of the overall system 10. The control system 50 comprises a processor 51 which runs a stored digital program that controls the overall operation of the system 10, a process control module 53 which is an interface between the processor 51 and the remaining components of the system 10, and a display 55 which provides a read out of the sampling results and the condition or current status of the system 10. The actuator and interface units module 60 is a collection of a plurality of control units which convert the control signals from the processor system 51 into electrical signals that operate the various actuators utilized by the system 10. The power unit 70 is utilized by all components of the system 10 as a power source. The power unit 70 provides power to the control system 50, the actuator and interface units 60, the PCAD 35 and the VCAD 45. Additionally, FIG. 1B illustrates the use of the various analyzers 80 and 90 that are used in conjunction with the PCAD 35 and the VCAD 45.

As is illustrated in FIG. 1B, the PCAD 35 is connected to an ion mobility spectrometer and gas chromatograph/electron capture detector combination 80. In the preferred embodiment only an ion mobility spectrometer is utilized; however, the gas chromatograph/electron capture detector can be utilized instead or a combination of the two can be utilized. The VCAD 45 is connected to a gas chromatograph/ electron capture detector and ion mobility spectrometer combination 90. In the preferred embodiment only a gas chromatograph/electron capture detector is utilized; however, the ion mobility spectrometer can be utilized instead or a combination of the two can be utilized. It is important to note that more than one electron capture detector may be utilized with a single gas chromatograph. If multiple electron capture detectors are utilized, they can be cascaded.

The gas chromatograph is a device utilized to separate the molecules of the volatile compounds for detection over time.

The device utilizes a separation technique which involves the passage of a gaseous moving phase through a volume containing a fixed absorbent phase. Gas chromatography is used primarily as a quantitative analytical technique. The gas chromatograph is typically used in conjunction with a final detection device such as an electron capture detector which is an ionization chamber that is used to determine the presence of certain ions. The ion mobility spectrometer is a device which ionizes and detects sample molecules so as to identify particular molecules by their time of arrival at the detector.

SAMPLING CHAMBER

The sampling chamber portal for people is a portal that is designed in such a way that as a person walks through this chamber, at a normal walking pace, an internal air flow carries a sample of vapors and/or particulate matter from them to a sampling port where it will be collected for analysis. There are three major design requirements that the chamber was designed to meet. First, the sampling chamber portal must gather a meaningful sample of the environment surrounding a person or object passing through the chamber. In considering a solution to the problem posed by the first design requirement, it is necessary to consider that the sampling chamber portal must be large enough for an average size individual to comfortably pass through the chamber; therefore, there is a considerable volume of air located within the chamber resulting in possibly only several parts vapor or particulate per trillion parts of air or possibly even less. The solution to this problem of dilution is to design the chamber long enough so the individual or object passing through the chamber remains in the chamber for a duration of time so as a meaningful sample of the environment can be gathered. Second, for the purposes of sensitivity, selectivity and preventing cross-contamination of the sample to be analyzed, the sample to be collected must be isolated as much as possible from the ambient environment. In considering a solution to the problem posed by the second design requirement, it is necessary to once again consider the problem of dilution caused by having a larger chamber. Since there already exists a dilution problem, the chamber must be designed with a unique geometry and internal aerodynamics so as to prevent further dilution and contamination by the mixing of internal air with the ambient air to the greatest extent possible. The third design requirement is that the sample must be gathered in as complete form as possible in as short as time as possible. In considering a solution to the problem posed by the third design requirement, it is necessary to consider the problems and solutions considered above and find a balance between them. The time an individual or object spends in passing through the chamber must be long enough so as to gather a meaningful sample, but not long enough to cause unduly long pedestrian traffic delays. Secondly, since there is a dilution problem, the chamber was designed in a unique way so as to prevent cross-contamination with the ambient environment, and this unique design must not prevent the normal flow of traffic; therefore, the aerodynamics discussed in the solution to the second problem must be such that the meaningful sample is gathered quickly.

Figure 3:
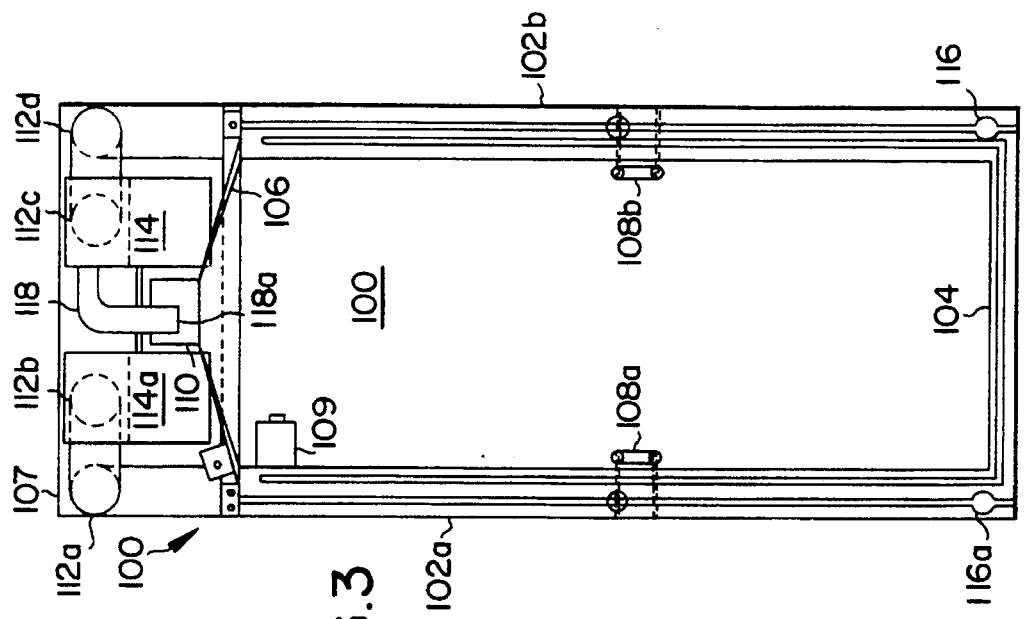
FIG. 3 is a sectional end view of the sampling chamber portal of the present invention taken along section lines 2—2' in FIG. 1.
Figure 2:
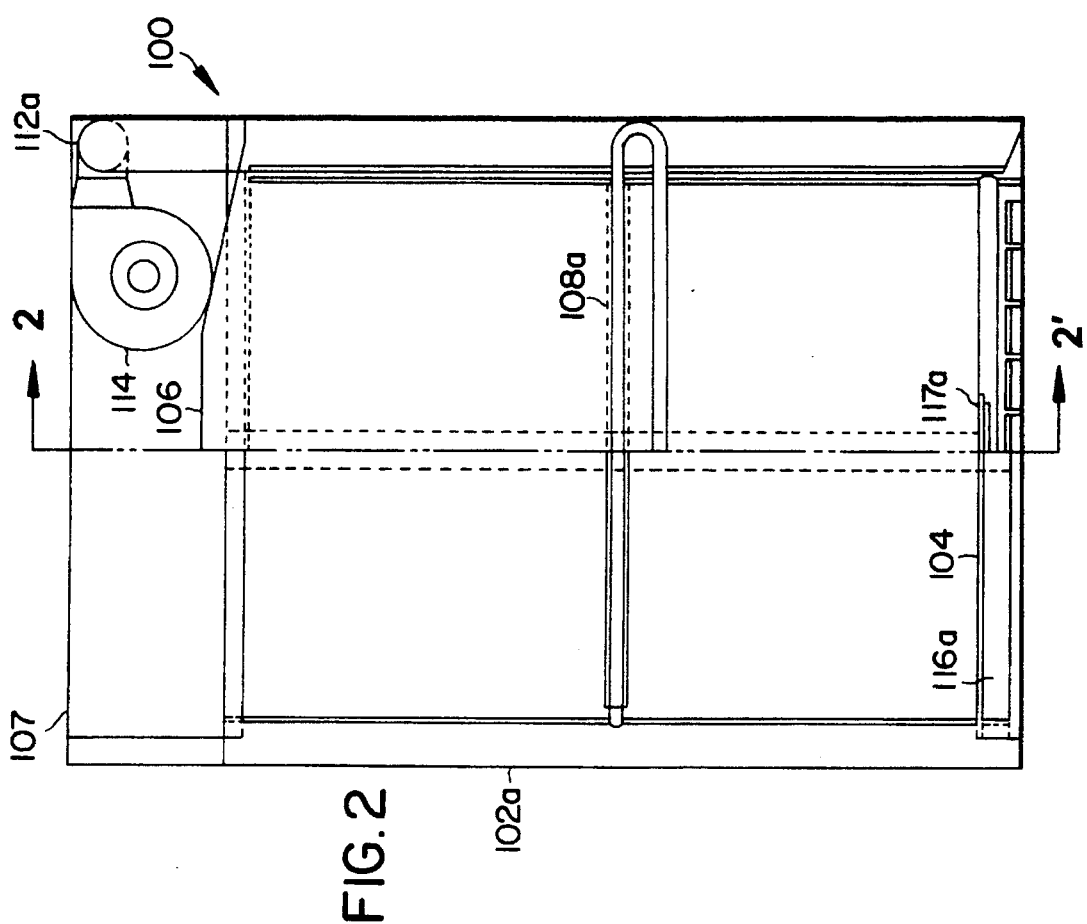
FIG. 2 is a sectional side view of the sampling chamber portal of the present invention.

Referring to FIGS. 2 and 3, there is shown a sectional side view and end view of the sampling chamber portal 100. The sampling chamber portal 100 has a rectangular geometry having internal dimensions of approximately six feet in length, seven feet in height, and three feet in width. These dimensions allow an average size individual, walking at an normal walking pace to remain in the chamber 100 for approximately two to three seconds which is enough time to gather the aforementioned meaningful sample. The rectangular chamber 100 has two walls 102a and 102b, which run the length of the chamber 100, a floor 104, a convergent or conically shaped ceiling 106 the importance of which will be discussed subsequently and a roof 107. In order to maintain the uninhibited flow of pedestrian traffic through the chamber 100, no doors and only two walls, 102a and 102b, were used. Hand rails 108a and 108b attached to walls 102a and 102b respectively are provided to aid individuals in passing through the chamber 100 quickly and safely. The floor 104 of the chamber 100 is not a necessary component, and in other configurations it is not utilized. The chamber 100 can be constructed utilizing a variety of materials including aluminum and plastics; however, clear materials such as plexiglass or fiberglass is preferred so individuals passing through the chamber 100 can be observed. In addition, a video camera 109 or even an electronic still picture camera may be utilized to capture an image of the individual passing through the chamber 100 which will be electronically stored along with the collected data.

The sampling chamber portal 100 operates on an air recirculating principle and the only air removed from the internal recirculating volume is a comparatively small amount leaving by sampling port 118a. The internal air volume is circulated through internal air flow guides or jets and is collected by collection duct 110 which is a 16 inches×20 inches×6 inches rectangular duct connected to the center of the conical ceiling 106 and which empties into the space created between the ceiling 106 and the roof 107. This results in a large volume of controlled recirculating air flow capable of delivering a vapor and/or particulate sample from anywhere in the chamber 100 to the sampling port 118a in approximately one second.

The conical ceiling 106 aids in the collection of the sample volume by creating an inverted funnel for the air sample flow which serves to concentrate a larger volume of air across a smaller cross section for sampling purposes. A dynamic low pressure zone is created in the region of the collection duct 110 when the air is drawn through the collection duct 110 into the ceiling plenum by four exhaust fans two of which are shown in FIG. 2 as 114, and 114a. In each corner of the chamber 100, there are six inch diameter end columns 112a–d. Each of the four end columns 112a–d are mounted vertically in the chamber 100 and run from the floor 104 to the ceiling 106. Each column 112a–d has six slots of one foot in length and a half inch in width with inch and a half internal guide vanes (not shown) for directing the air flow at a forty-five degree angle towards the center of the chamber 100. The air flow through the columns 112a–d is provided by four independent fans, two of which are shown in FIG. 2 as fans 114 and 114a. The four fans are mounted in the chamber 100 above the conical ceiling 106 and below the outer roof 107. Each fan is connected to one of the end columns 112a–d and provide 1000 CFM of air to each column 112a–d. The suction side of the fans are open to a common plenum located in the same space that the fans occupy. In addition to these inwardly directed vertical air jets 113a–d there are two upwardly directed air guides or jets located in side air flow pipes 116a and 116b which are mounted along the floor 104 and against walls 102a and 102b. The side flow pipes 116a and 116b are connected to end columns 112a–d and receive air from them. In each side flow pipe 116a and 116b there are twelve inch by half inch air slots one of which is shown as 117a, located in the center of each pipe and directed towards the center of the chamber at a forty-five degree angle as shown in FIG. 2. The combined effect of the air flow created by the end columns 112a–d and the side flow pipes 116a and 116b is a dynamic high pressure region created in the center region of chamber 100. The recirculating fans which draw air through collection duct 110 create a dynamic low pressure zone within chamber 100, which creates a net air flow up towards the collection duct 110. This air flow is the flow that sweeps individuals or objects passing through the chamber. The effect of the high pressure region and the low pressure region created by the exhausting of the air sample through conical ceiling 106 and into the collection duct 110 is a balance of atmospheric conditions which results in very little external air entering or leaving the chamber 100. Basically, the high pressure region inhibits air from entering the chamber 100. The majority of the moving air mass goes through the collection duct 110 and to the common plenum where it will once again be used by the four fans to recirculate the internal volume of the chamber 100. A portion of the recirculated air is collected through a sampling port 118a, which is the open end of a pipe 118 which is used to transport a selected sample from the chamber 100 to the second stage of operation; namely, the preconcentration and vaporization stage which shall be discussed subsequently. The pipe 118 which is presently utilized is constructed of ABS plastic; however any suitable piping material may be used such as stainless steel.

The four end columns 112a–d and the two side air flow pipes 116a and 116b represent one embodiment for delivering the air supplied by the four independent fans as separate and directional air jet streams. The fans can be connected to various types of air ducts or plenums with guide vanes or nozzles to form the exiting air into jet streams. In addition, partitioned hollow walls also with guide vanes or nozzles can be used as an alternate approach for forming the air from the fans into separate and directional air jet streams. The manner in which the air flow is supplied to the guide means and the manner in which the jet streams are formed is not critical; however, the specific directions of the jets streams are. It is important that the proper angle and orientation of the jet streams be maintained so as to provide a net flow of air capable of sweeping an individual or object passing through said sampling chamber means 100 while maintaining the integrity of the volume of air within the sampling chamber means 100.

HAND-HELD WAND

The hand-held wand is a device for gathering a sample volume of air from a specific area on an individual or object and for removing particulate matter from the individual or object and introducing the particulate matter into the sample volume of air while preventing undue contamination of the sample volume of air from the ambient environment. Whereas the sampling chamber portal gathers vapors surrounding an individual and sweeps particulates from the individual, the hand-held wand gathers a more concentrated sample volume of air containing vapors and particulate matter from a specific area on the individual or object.

Figure 4:
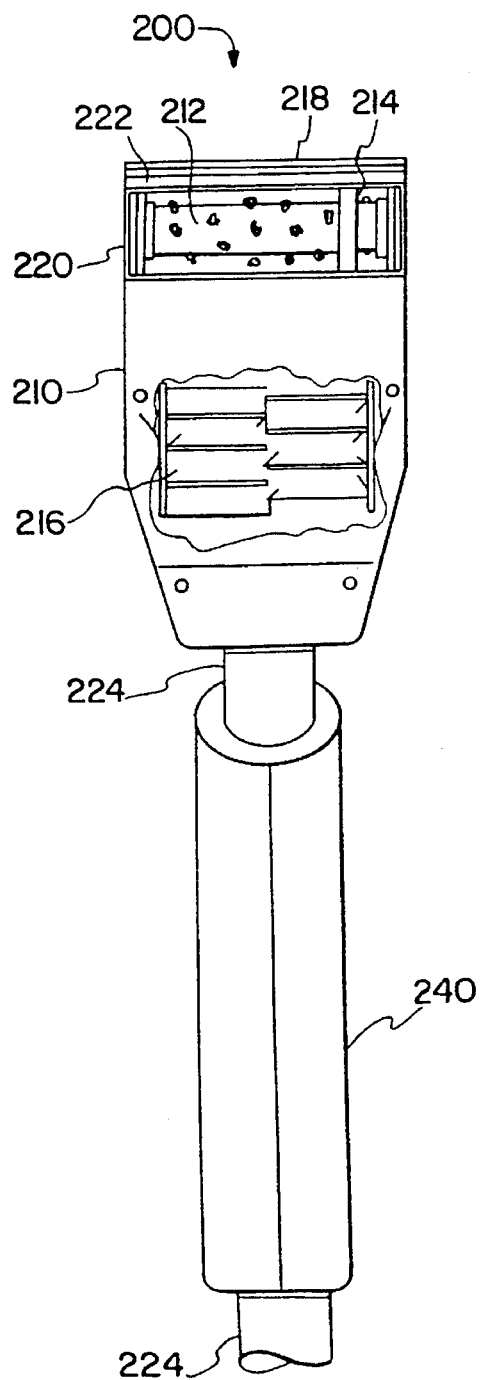
FIG. 4 is an under-side view of the hand-held wand of the present invention.

Referring to FIG. 4, there is shown the under-side view of the hand-held wand 200. The hand-held wand 200 basically comprises two main sections, the head 210 and the handle 240. The head 210 and the handle 240 are connected by a swivel joint 223 that allows the head 210 to pivot into hard to reach places or accommodate difficult angles. The head 210 comprises a rotating brush 212 disposed within the inlet port 214 of the head 210. The rotating brush 212 is utilized to sweep and remove particulate matter attached to an individual or an object. The rotating brush 212 is driven by an air turbine 216 via a belt drive 218. The air turbine 216 is located towards the outlet end of the head 210 and is driven by the flow of air over the turbine blades of the turbine 216. The air flow which drives the turbine 16 is caused by a suction fan located in the second sample collection and analytical subsystem. This suction fan is utilized to draw the sample volume of air during a sampling period. A complete description of the sampling procedure is given in detail in subsequent sections. The effect of the sweeping action and the drawing of the sample volume of air combines to create a sample volume of air containing both vapors and particulate matter.

It is important to note that some of the various materials of interest leave "sticky residues" or "sticky particulates" on the individuals or objects that come in contact with these materials; therefore, in order to remove them, it is necessary to physically sweep them from the individual or object.

The "sticky particulates" are from a particular class of target materials; namely, plastic explosives such as the military high explosive C4, DM-12, and SEMTEX. It is important that these particulates be collected because they exhibit extremely low vapor pressures, and are therefor not detectable with vapor detectors. Typically, these explosives have vapor pressures of 10,000 to 1,000,000 times lower than conventional explosives. Therefore, if the particulates themselves are not collected, it is virtually impossible to detect the presence of these explosives. These particular explosives cannot be handled without the sticky residue remaining on whatever comes in contact with the explosives. A complete description of this phenomenon is given in the Analysis section.

The suction fan utilized to draw the sample volume of air is capable of developing a flow rate of 70 to 85 CFM. This flow rate translates into a vacuum capable of raising 115 to 140 inches of water when the hand-held wand 200 is sealed against the side of a piece of luggage, and a vacuum capable of raising 33 to 40 inches of water when the hand-held wand 200 is opened to the ambient environment through a one inch orifice. Through experimentation, it has been established that this vacuum enables the hand-held wand 200 to draw vapors through the side of cloth and vinal suitcases as well as through the sidewalls of plastic bags in which explosives have been concealed. The determination of whether a meaningful sample of vapors has been gathered depends upon the concentration of the initial sample and the porosity of the particular container.

The inlet port 214 comprises edges 220 formed of a rigid material such as a hard plastic or metal. These edges 220 are attached to the inlet port 214 by a spring loading mechanism in such a manner that allows the edges 220 to be pushed into crevices on an individual or object. This enables a sealing edge 222 of soft elastomeric material located on the outside perimeter of the edges 220 to be brought into contact with the object to provide a vacuum seal that prevents contamination of the sample volume of air by the ambient environment.

The head 210 is connected to the handle 240 through a conduit 224 and swivel joint 223. As is stated previously, this joint is a swivel connection that allows for greater accessibility of the head 210 to certain locations. The conduit 224 runs through the length of the handle 240 and is flexible thereafter. It connects the hand-held wand 200 to the first and second sample collection and analytical subsystems and to transport the sample volume of air collected to these subsystems for preconcentration and/or vaporization, which as stated previously will be discussed. subsequently. The union between pipe 224 and the handle 242 may also be a swivel connection to allow a greater freedom of movement.

Figure 5:
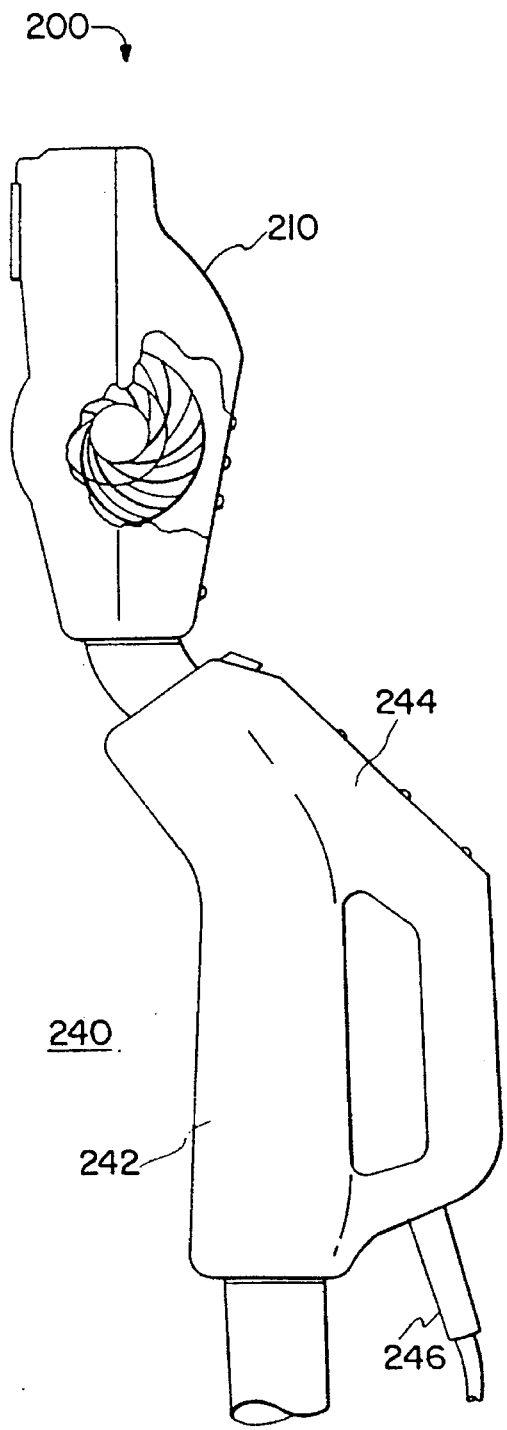
FIG. 5 is a side view of the hand-held wand of the present invention.
Figure 6:
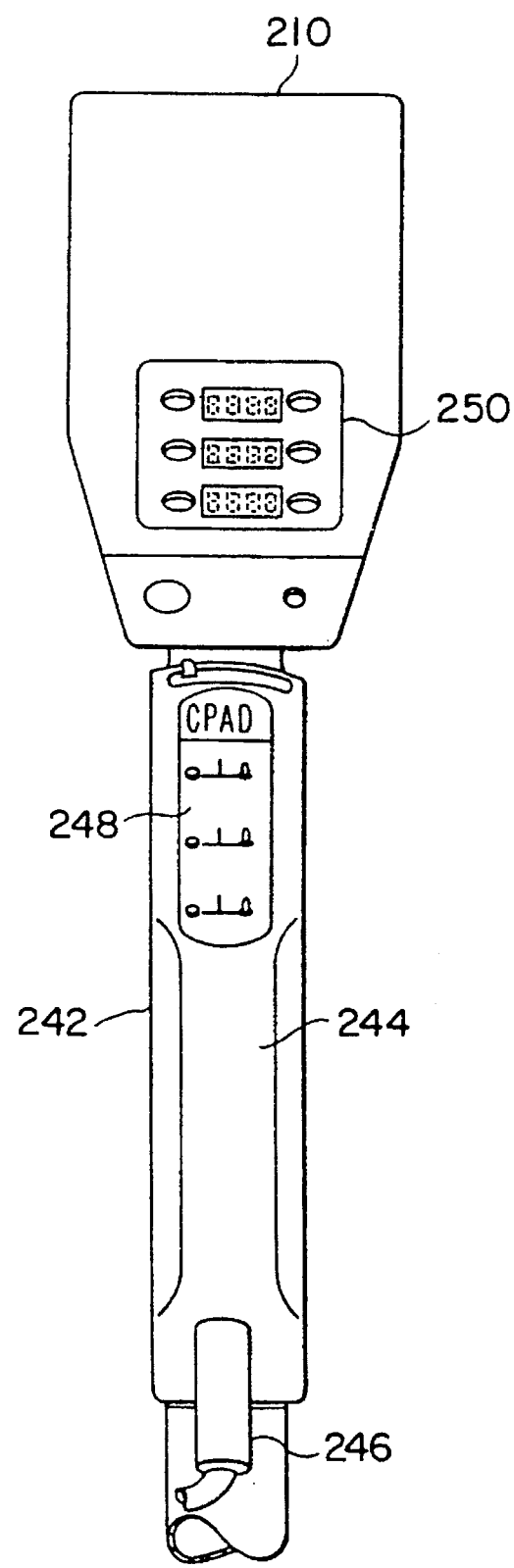
FIG. 6 is a top view of the hand-held wand of the present invention.

Referring to FIG. 5, a side view of the hand-held wand 200 is shown to better illustrate the design of the handle 240. The handle 240 comprises a main section 242 through which the pipe 224 runs through, and a grip section 244 by which the user holds onto. A control cable 246 runs through the grip section 244 and carries all the control and signal display wires from the control and data processing system, to be discussed subsequently, to the controls and displays of the hand-held wand 200. FIG. 6 illustrates a top view of the hand-held wand 200 and shows the control panel 248 and the display panel 250. The controls and displays may utilized to operate the detection screening system from a remote location.

The control panel 248 comprises control switches used to actuate a single cycle function, a continuous cycle function, a pause function and the reset function of the detection and screening system. The single cycle, continuous cycle, and pause functions are associated with the collection of the target materials. The reset function is utilized to reinitialize the system after an alarm condition. The display panel 250 comprises an alarm display area and a numeric display area. The alarm display area is used to indicate whether a target material has been detected by the first sample collection and analysis subsystem, the second sample collection and analysis subsystem or both. Additionally, the alarm display comprises an audio alarm which indicates to the system user that a target compound has been detected. The numeric display area is normally used to display an identification number associated with the sample being taken, but may also be used to display the identification number of the sample which triggered the alarm.

AUTOMATED BAGGAGE/PARCEL SAMPLING CHAMBER

The automated baggage/parcel sampling chamber is a device for gathering a sample volume of air surrounding an object and for removing particulate matter from all exposed surfaces of the object and introducing the particulate matter into the sample volume of air. Like the hand-held wand, the automated baggage/parcel sampling chamber gathers a more concentrated sample volume of air containing vapors and particulate matter than the sampling chamber portal. As is the case with the hand-held wand, the automated baggage/parcel sampling chamber has means for gathering the sample of volume of air directly from the object.

Figure 7:
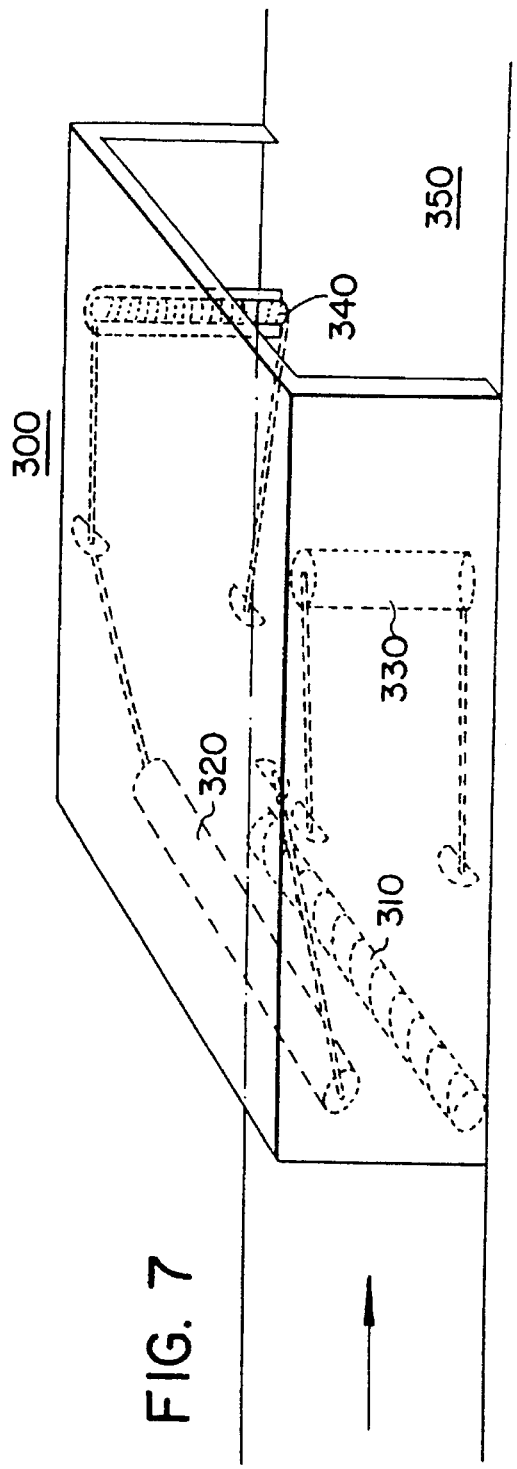
FIG. 7 is a diagrammatic representation of the automated baggage/parcel sampling chamber of the present invention.

Referring to FIG. 7, there is shown the basic configuration of the automated baggage/parcel sampling chamber 300. The automated baggage/parcel sampling chamber 300 is a rectangular open ended tunnel structure. The size of the cheer 300 may vary, however, for convenience the size of the chamber 300 is chosen to match that of a baggage scanning x-ray device of the kind used in airports today. In this embodiment, the automated baggage/parcel sampling chamber 300 is approximately six feet in length, 38 inches in width and 32 inches in height. The automated baggage/parcel sampling cheer 300 is fitted over a conveyor belt 350 which is utilized to carry the baggage or parcels through the chamber 300 at a rate of speed that would enable the baggage or parcels to be sampled for a duration ranging between approximately three to seven seconds although the range may be extended if desired. The automated baggage/parcel sampling chamber 300 also comprises at least four automated sampling heads 310, 320, 330, and 340 which are utilized to gather the sample volume of air.

Figure 8:
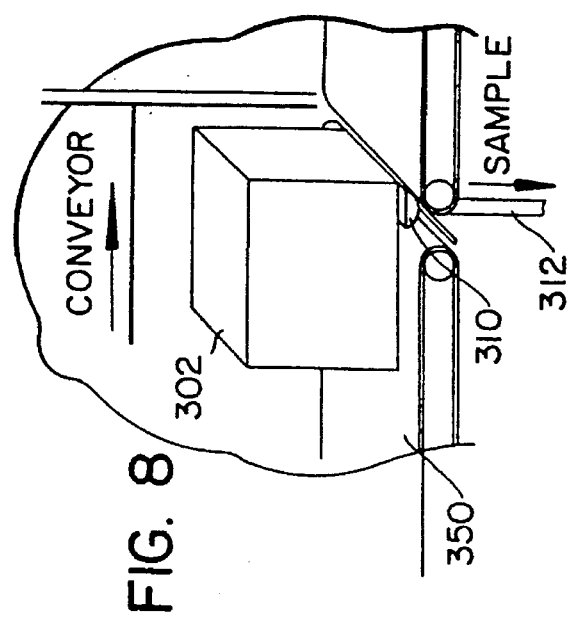
FIG. 8 is a diagrammatic representation of the automated baggage/parcel sampling chamber and first automated sampling head of the present invention.

The four automated sampling heads 310, 320, 330, and 340 each contain rotating brushes which are utilized to remove the "sticky" particulates from the luggage or other object of interest. The first automated sampling head 310 is located at the entrance of the chamber 300 immediately before the conveyor belt 350 as shown in FIG. 8. The inlet of the first automated sampling head 310 extends the entire width of the chamber 300 and is set so that the rotating brush gently sweeps and draws vapors and particulates from the bottom of the baggage or parcel 302 as it is pushed onto the conveyor belt 350. As was stated previously, the various materials of interest leave a "sticky residue" on the objects they come in contact with, and thus it is necessary to sweep the particulate matter from the object. The first automated sampling head 310 is valve connected to a common plenum (not shown) through a pipe or conduit 312.

Figure 9:
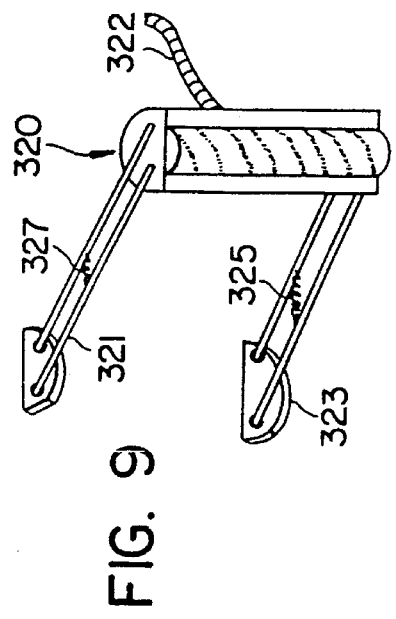
FIG. 9 is a diagrammatic representation of the automated baggage/parcel sampling chamber and second automated sampling head of the present invention.

The second automated sampling head 320 is hingedly connected to the roof of the sampling chamber 300 inside the entrance of the chamber 300. A representation example of a typical sampling head 320 is shown in FIG. 9. The inlet of the second automated sampling head 320 extends the entire width of the sampling cheer 300, and as the baggage or parcel 302 moves through the sampling chamber 300, the second sampling head 320 sweeps and draws vapors from the top portions of the baggage or parcel 302. The second automated sampling head 320 is connected to the roof of the sampling chamber 300 by two pairs of paralever arms 321 and 323. First and second offset springs 325 and 327 are attached between each set of paralever arms 321 and 323 in order to bias the sampling head into the path of the luggage, and provide tension between the sampling head 320 and the baggage or parcel 302 as it travels through the chamber. The offset springs 325 and 327 maintain the second automated sampling head 320 in firm contact with the baggage or parcel 302 as the paralever arms 321 and 323 are forced upward. The second automated sampling head 320 is valve connected to the common plenum through a pipe or conduit 322.

Figure 10:
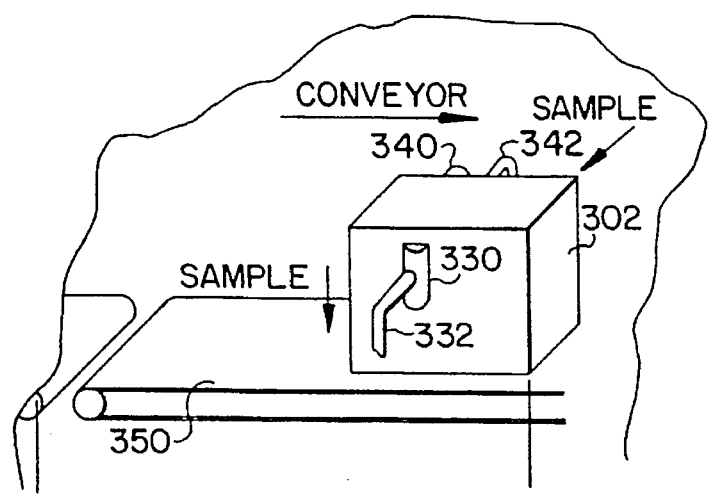
FIG. 10 is a diagrammatic representation of the automated baggage/parcel sampling chamber and third and fourth automated sampling heads of the present invention.

As illustrated in FIG. 10, the third and fourth automated sampling heads 330 and 340 are hinged connected on opposite sides of the sampling chamber 300 so as to not interfere with the second automated sampling head 320. The third and fourth sampling heads 330 and 340 automatically adjust to the width of the baggage or parcel 302, by spring loading or by the use of sensors and servos (not shown), in a manner such that the sides of the baggage or parcel 302 are gently swept by the sampling heads. The third and fourth sampling heads 330 and 340 are valve connected to the common manifold through pipes or conduits 332 and 342.

The sampling of a piece of baggage or parcel involves three sampling sequences. First, the baggage or parcel 302 moves across the first automated sampling head 310 located at the entrance of the sampling chamber 300. During this process, the suction and air flow generated by the suction fan located in the second sample collection and analytical subsystem is totally dedicated to this sampling head 310. The valve system (not shown) at this sampling step provides for the valve for sampling head 310 to be open to the common manifold while the valves to the remaining sampling heads 320, 330, and 340 are closed. At the second sampling step, the second automated sampling head 320 is activated. When the baggage or parcel reaches a set point in the sampling chamber 300, the second sampling head 320 is activated by its sensor. A valve (not shown) controlling the air flow to the common manifold is opened and the valve leading to the second automated sampling head 320 is opened while the valves associated with the remaining sampling heads 310, 330, and 340 are closed. The air flow and suction is now totally dedicated to the second automated sampling head 320. At the third and final step, the third and fourth sampling heads 330 and 340 are activated. When the baggage 302 or parcel reaches another set point in the sampling chamber 300, the third and fourth sampling heads 330 and 340 are activated by the dedicated sensor. At this final stage, the valving system provides for air flow and suction only from these two automated sampling heads 330 and 340. As the baggage 302 or parcel is moved forward on the conveyor belt 350, the third and fourth sampling heads 330 and 340 close in on the sides of the baggage 302, and gently brush and draw in vapors and particulates.

The vacuum fan utilized to draw the sample volume of air is capable of developing a flow rate of 70 to 85 CFM at each sampling head, which enable the sampling heads to draw vapors through the seams and closure joints of the baggage. It will also draw vapors through cloth and vinal suitcases as well as through the plastic material used to conceal explosives. The determination of whether a meaningful sample of vapors has been gathered depends upon the concentration of the initial sample and the porosity of the particular container.

The common manifold (not shown) is connected to the first and second sample collection and analytical subsystems. In one embodiment, the sample volume of air collected by each automated sampling head 310, 320, 330, and 340 is directly sent to the first and second sample collection and analytical subsystems, and thus three separate analysis' are done on a particular piece of baggage 302. In a second embodiment, the sample volumes of air collected by all four automated sampling heads 310, 320, 330, and 340 can be gathered and then released to the first and second sample collection and analytical subsystems for a single analysis.

FIRST SAMPLE COLLECTION AND ANALYTICAL SUBSYSTEM

Figure 11A:
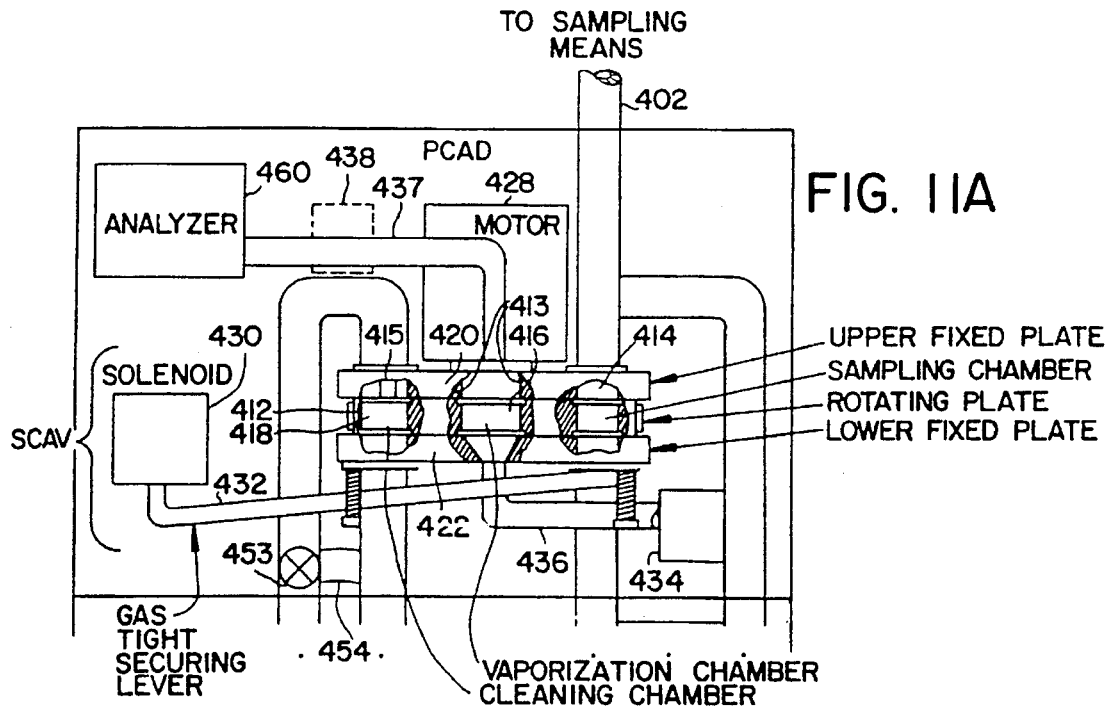
FIG. 11A is a diagrammatic representation of the first sample collection and analysis subsystem of the present invention.

The first sample collection and analysis subsystem 400, shown in FIG. 11A, is the particulate collector and detector. It is located in line between the sampling means, which is either the walk through sampling chamber portal, the handheld wand, or the automated baggage/parcel sampling chamber, and the second sample collection and analysis subsystem 500. The PCAD 400 is comprised of the sample collector and vaporizer 410 and the chemical analyzer 460 which may be either a gas chromatograph/electron capture detector(s), GC/ECD, or an ion mobility spectrometer, IMS or both. The PCAD 400 is used to collect and analyze particulates in a sample volume of air collected in one of the three sampling means for the chemical compounds of interest. This is accomplished by first collecting and converting the particulates to vapor in the SCAV 410 and then submitting the vapors to the chemical analyzer 460 for analysis. A description of the SCAV 410 operating in conjunction with both types of chemical analyzers 460 is given in the following paragraphs.

SAMPLE COLLECTOR AND VAPORIZER (SCAV)

The SCAV 410 is located in line between either of the three sampling means and the second sample collection and analysis subsystem 500. The SCAV 410 is used to collect and vaporize particulate samples from an air stream as it moves from one of the three sampling means through the PCAD 400 and on to the second sample collection and analysis subsystem 500. The SCAV 410 is supplied with the air stream by a pipe 402 which extends and connects to either of the three sampling means. During sampling periods a high suction fan 404 draws the sample volume of air from one of the three sampling means thereby causing the air stream to flow into the SCAV 410. The suction fan 404 is connected to pipe 402 on the suction side, and the discharge of the fan 404 is connected to a vent or exhaust system to the ambient environment.

Figure 12:
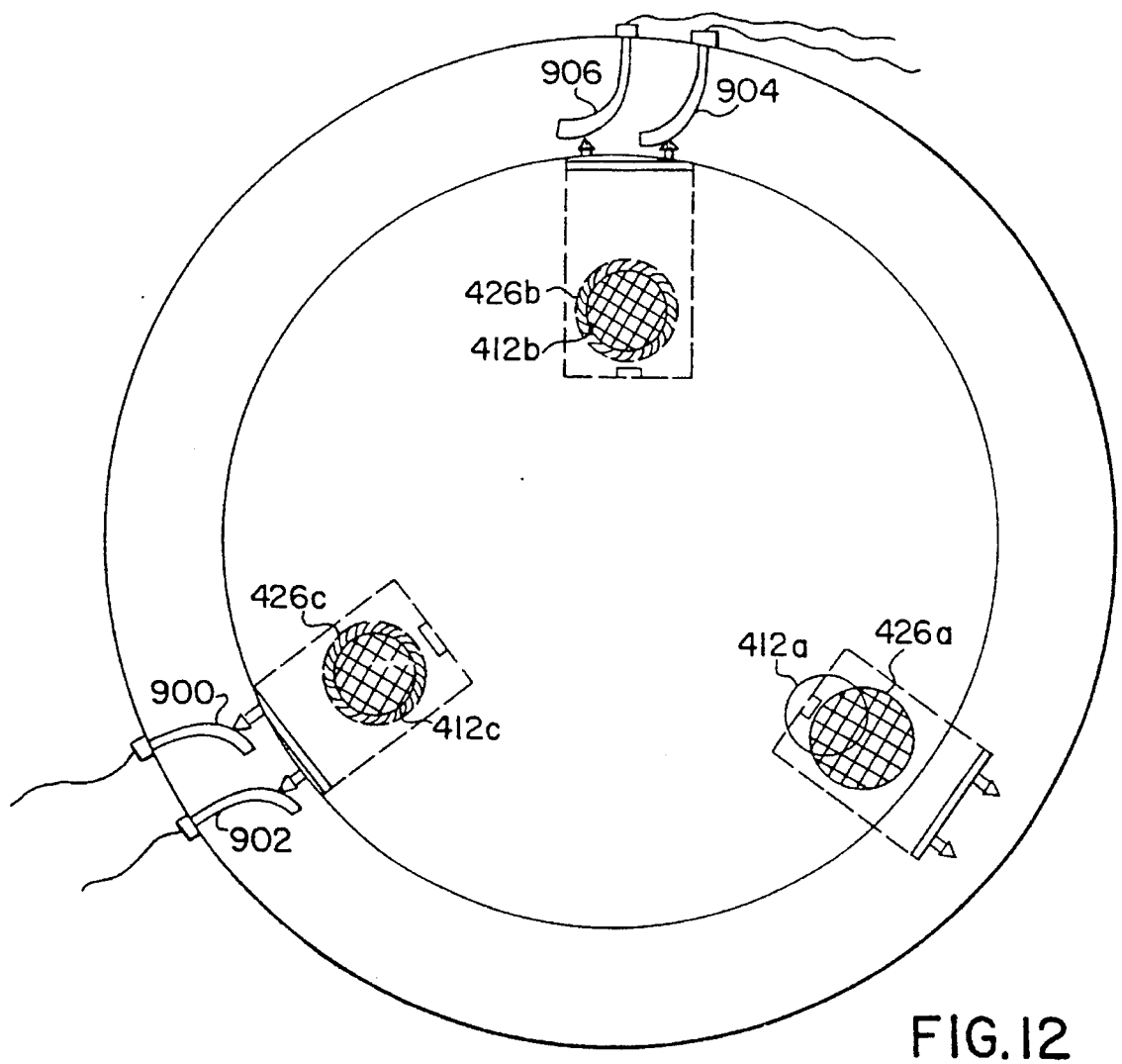
FIG. 12 is a diagrammatic representation of the filter element configuration utilized in the first sample collection and analysis subsystem of the present invention.

The SCAV 410 comprises a rotating circular plate 412, a collection chamber 414, a vaporization chamber 416, and a cleaning chamber 418. The collection, vaporization and cleaning chambers 414, 416, and 418 are formed from the union of first and second fixed SCAV plates 420 and 422. The first and second fixed SCAV plates 420 and 422 each comprise approximately one half of the volume of each of the three chambers 414, 416, and 418. The first and second fixed SCAV plates 420 and 422 are aligned such that the collection chamber 414, the vaporization chamber 416 and the cleaning chamber 418 are configured 120 degrees apart from each other. The rotating circular plate 412 is disposed between the first and second fixed plates 420 and 422 and is mounted for rotation therebetween. The rotating circular plate 412 has three circular holes 412a, b and c equally spaced 120 degrees apart and covered with three mesh filter elements 426a, b and c. The configuration of the three filter elements 426a, b and c on the rotating circular plate 412 is shown in FIG. 12. The rotating circular plate 412, is rotated by a motor 428, through 120 degrees of rotation during every sampling period so that each of the mesh filter elements 426a, b, and c occupies one of the collection chamber 414, the vaporization chamber 416 or the cleaning chamber 418 during any given sampling period. The motor 428 utilized to rotate the rotating circular plate 412 is a gear head motor which is controlled by the PCAD actuator unit which is an integral part of the control and data processing system to be described in detail in subsequent paragraphs. A stepper motor can also be utilized. On completion of each rotation, a lever mechanism 432, which is actuated by a solenoid 430, pulls the first and second fixed SCAV plates 420 and 422 together so that each of the three filter elements 426a, b, and c are sealed in either of the three chambers 414, 416, and 418 during a particular sampling period. The solenoid 430 and the lever mechanism 432 are controlled by the PCAD actuator unit. The three filter elements 426a, b, and c are completely sealed, in an air tight fashion, in each of the three chambers 414, 416, and 418. The air tight seal is accomplished by an O-ring seal which surrounds each of the three chambers 414, 416, and 418. The O-ring seals are placed around the perimeter of the chambers, or more accurately, around each of the half chambers in each of the first and second fixed SCAV plates 420 and 422. To completely illustrate the design and operation of the SCAV 410, a complete 360 degree rotation of the rotating circular plane 412 is described.

To illustrate the three sampling periods which corresponds to one 360 degree rotation of the rotating circular plate 412, it is necessary to state or assume that filter element 426a is inside the collection chamber 414, filter element 426b is inside the vaporization chamber 416, and filter element 426c is inside the cleaning chamber 418 at the system start-up time. In this position, the filter element 426a and hole 412a are directly in line with pipe 402 and thus filter element 426a is capable of selectively collecting, or more precisely, physically trapping target particulates which are drawn from any of the three sampling means during a sampling period. The particulate matter drawn in is physically trapped or adsorbed on filter element 426a. A complete description of the filter elements 426a, b and c are given in subsequent paragraphs. Vapors collected by any of the three sampling means pass through the filter element 426a and proceed directly to the second sample collection and analysis subsystem 500 for concentration. The filter elements 426a b, and c can be varied in mesh size so as to be able to collect specific size particulates and still allow vapors to pass easily therethrough. Upon completion of this first sampling period, the solenoid 430 is actuated by the control and data processing system thereby causing lever mechanism 432 to separate the first and second fixed SCAV plates 420 and 422. Once the separation of the first and second fixed SCAV plates 420 and 422 is completed, the gear head motor 428 is engaged by the PCAD actuator unit of the control and data processing system and rotates the circular plate 412 120 degrees, placing filter element 426a, with trapped particulates, inside the vaporization chamber 416 while filter element 426b is placed inside the cleaning chamber 418 and filter element 426c is placed inside the collection chamber 414.

The vaporization chamber 416 is a sealed chamber which contains a pair of electrical terminals 413 which connect to filter element 426a when that particular filter element occupies the vaporization chamber 416. The pair of electrical terminals 413 provide a computer controlled current directly to the filter element 426a in order to generate a specific amount of ohmic heat energy to effectively vaporize the collected particulate matter. The current is controlled by the control and data processing system. Through experimentation, it has been established that a flash heat of 250 millisecond duration vaporizes the targeted materials and creates an instantaneous increase in gas pressure within the vaporization chamber 416 of very short duration which acts to aid in the vaporization and injection of a controlled volume of the sample into the chemical analyzer 460. As the flash heating and vaporization is taking place a small quantity of carrier gas from gas supply means 434 is continuously fed into the vaporization chamber 416 via gas line 436. The gas flow is used to sweep or carry the molecules from the vaporized particulates into the chemical analyzer 460. In the preferred embodiment, the gas utilized is an inert gas; however, other non-reactive gases can be utilized. In one embodiment, the vaporization chamber 416 is connected directly to the chemical analyzer 460 and the carrier gas sweeps the vaporized material or first sample volume directly into the chemical analyzer 460, and in a second embodiment, a three-way valve 438 is utilized as an interface between the vaporization chamber 416 and the chemical analyzer 460. Pipe 437 carries the sample volume from the vaporization chamber 416 to the chemical analyzer 460 either directly or through the three way valve 438.

FIG. 11D diagrammatically illustrates the analyzer 460 for the preferred embodiment of the PCAD unit. An ion mobility spectrometer 460 is equipped with a collector plate 461, a shutter grid 462, and a repeller plate 463 which are biased by a 3,000 volt bias source 464. The IMS device is made up of the sequential series of conducting and insulating rings which provide a voltage gradient across the drift region 465 in a conventional manner. A ring of nickel 63 466 is provided as the ionizing source in the middle of reaction chamber 467. Nickel 63 is a beta emitter that emits low energy electrons for ionization of molecules of interest vaporized in the PCAD unit.

The ion mobility spectrometer 460 illustrated in FIG. 11D is a high duty cycle device engineered to analyze a new sample every four to six seconds. While conventional mass spectrometers would be suitable for the PCAD analyzer at low duty cycles, the ion mobility spectrometer is a better choice for high duty cycles. The PCAD device is intended to analyze and detect minute particulates of plastic explosives such as C 4, DM 12 and Semtex which may be analytically identified by the RDX and PETN molecules therein. The plastic explosive particles, however, also include substantial amounts of polymers, oil, and plasticizers in addition to the explosive crystals, and in a high duty cycle environment, conventional GC/MS detectors may become packed with unwanted contaminants. In addition, conventional MS/MS and API/MS devices, which require a high vacuum for operation, may become saturated from the high duty cycle, and their accuracy impaired. In the ion mobility spectrometer of the present invention, the vaporized particulate matter is introduced through a tube 437 from the flash vaporization chamber 416 into the reaction chamber 467. The drift gas is introduced at the collector end of the device through port 468, and exhausted through exhaust port 469 along with the unwanted contaminants introduced by the particles of plastic explosive. In the reaction region 467, the vaporized sample is ionized by the nickel 63 ring and the ionized molecules are then admitted into the drift region 465 by the shutter grid 462. All non-ionized molecules, including most of the unwanted contaminants are evacuated through exhaust 469. This means that the walls of the drift region 465 remain relatively clean and uncontaminated by the high duty cycle since only the ionized molecules are introduced into the drift region.

When CPU 475 initiates process control 473 and the flash vaporization cycle, it also resets the sample and hold circuitry 472, which in turn initiates the grid pulse generator 470. The grid pulse generator 470 then sequentially pulses trigger grid 462 every 25 milliseconds to admit a new ion sample into drift region 465. The output of the collector plate 461 is amplified and converted to digital form by analog to digital converter 471 and the output thereof is passed to a sample and hold circuit 472. Sample and hold circuit 472 is initiated by process control 473 in synchronization with the flash vaporization in the PCAD unit.

In operation, a typical duty cycle includes at least a collection cycle and a vaporization cycle, and preferably a cleaning cycle, not illustrated in FIG. 11D. As illustrated in FIG. 11D, the filters 466, 467 are rotated between a collection chamber 414 and a flash vaporization chamber 416. When filter unit 466 is positioned within the collection chamber, it preferentially retains particulate matter in the matter hereinbefore described. When filter means 467 is positioned within the flash vaporization chamber 416, a supply of carrier gas is admitted through conduit 476 into the flash vaporization chamber 416. Process control 473 then initiates the flash vaporization by applying a direct electrical current to filter 467 to-thereby ohmically heat the filter in the matter hereinbefore previously described. The flash vaporization takes approximately 250 milliseconds and simultaneously vaporizes the collected particulate matter present on screen 467 while heating the surrounding carrier gas that has entered the chamber through conduit 476. As the gas and the flash vaporization chamber is heated, a pulse of high energy heated gas is created with the molecules of interest entrained therein, which pulse then travels through the injection means 437 into the reaction chamber 467 of analyzer 460. In this region, the molecules of interest are ionized and, every 25 milliseconds, another sample is admitted into the drift region 465. While the grid pulse generator 470 continuously pulses the trigger grid 462, the screen 467 is only heated once in a given duty cycle, or once every four to six seconds.

After process control 473 has initiated a flash vaporization of the sample, it delays the sample and hold circuitry 472 for approximately two seconds before sampling the output of the A to D converter 471. The sample and hold circuitry will be enabled for approximately one-half second, and during that one second, it will receive approximately 20 spectral sweeps or plasmagrams from collector plate 461 and A to D converter 471. As sample and hold circuit 472 samples the amplified output signal at collector plate 461 at periodic intervals, it averages them to form a digital pattern representative of the collected and averaged signals. At the end of the averaging period, the collected digital pattern is then compared by CPU 475 with other digital patterns stored in memory. If a match is found between the digital pattern in the sample and hold circuit 472 and one of the patterns at CPU memory, the CPU activates an alarm condition.

In a preferred embodiment, digital patterns for the spectra from RDX and PETN molecules are stored in CPU memory 475.

Figure 11B:
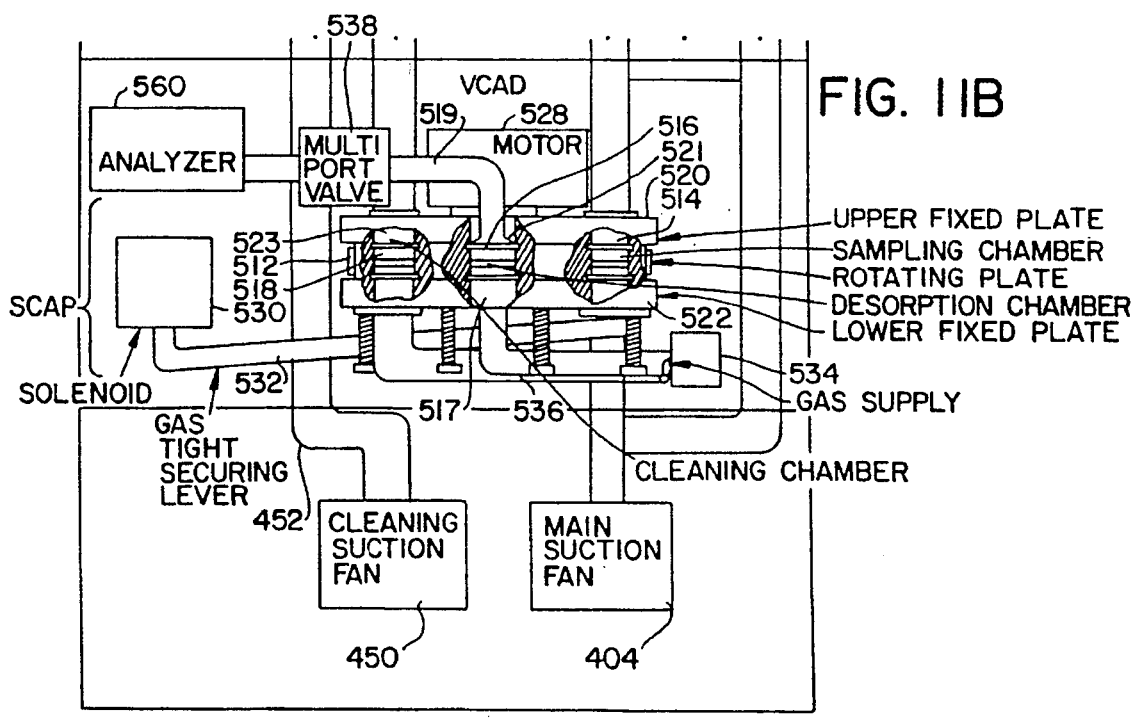
FIG. 11B is a diagrammatic representation of the second sample collection and analysis subsystem of the present invention.
Figure 11C:
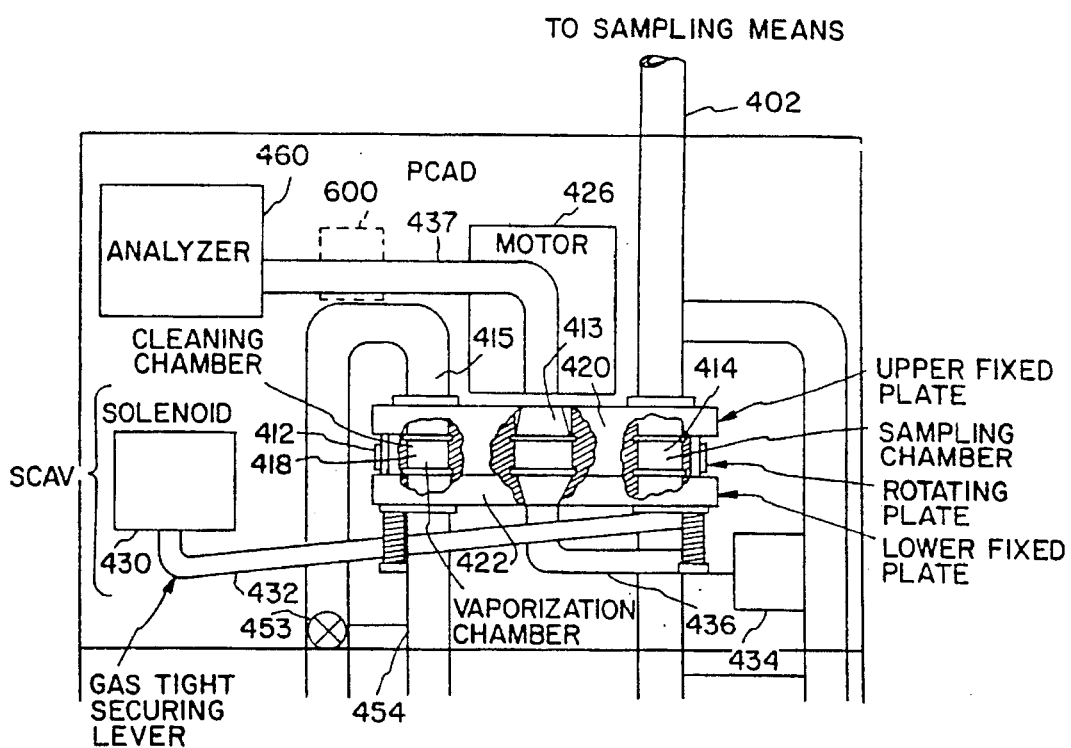
FIG. 11C is a diagrammatic representation of the first sample collection and analysis subsystem of the present invention, wherein the subsystem utilizes a six-port valve configuration.
Figure 13A:
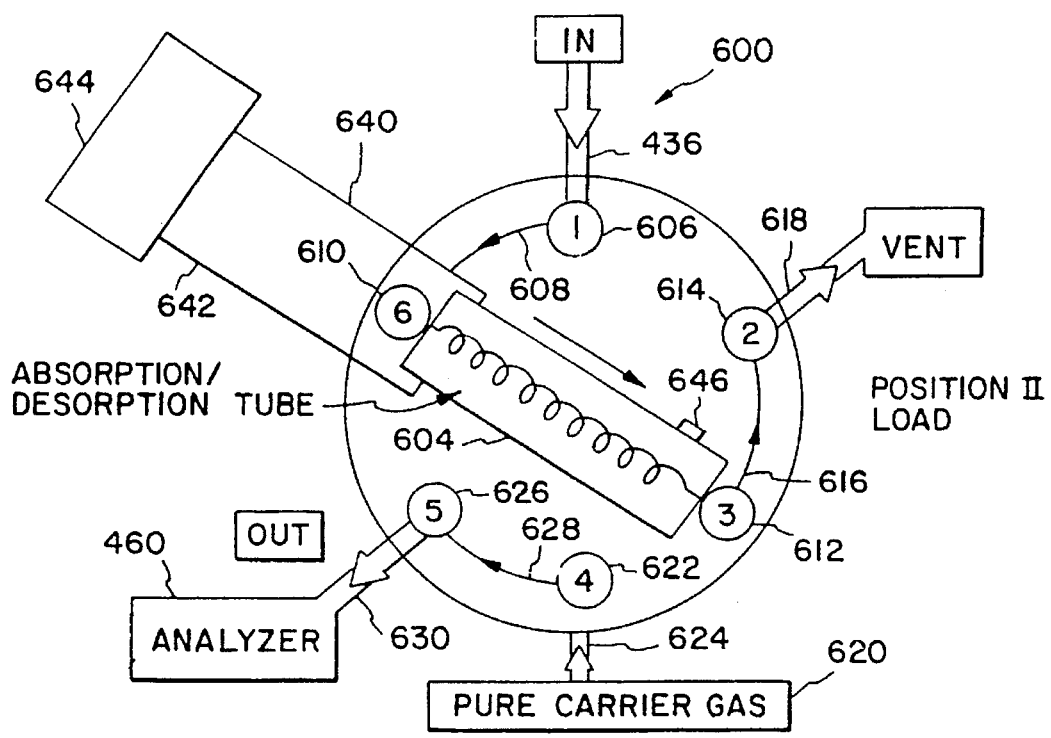
FIG. 13A is a diagrammatic representation of the six-port valve used in the present invention with the six-port valve in the load position.
Figure 13B:
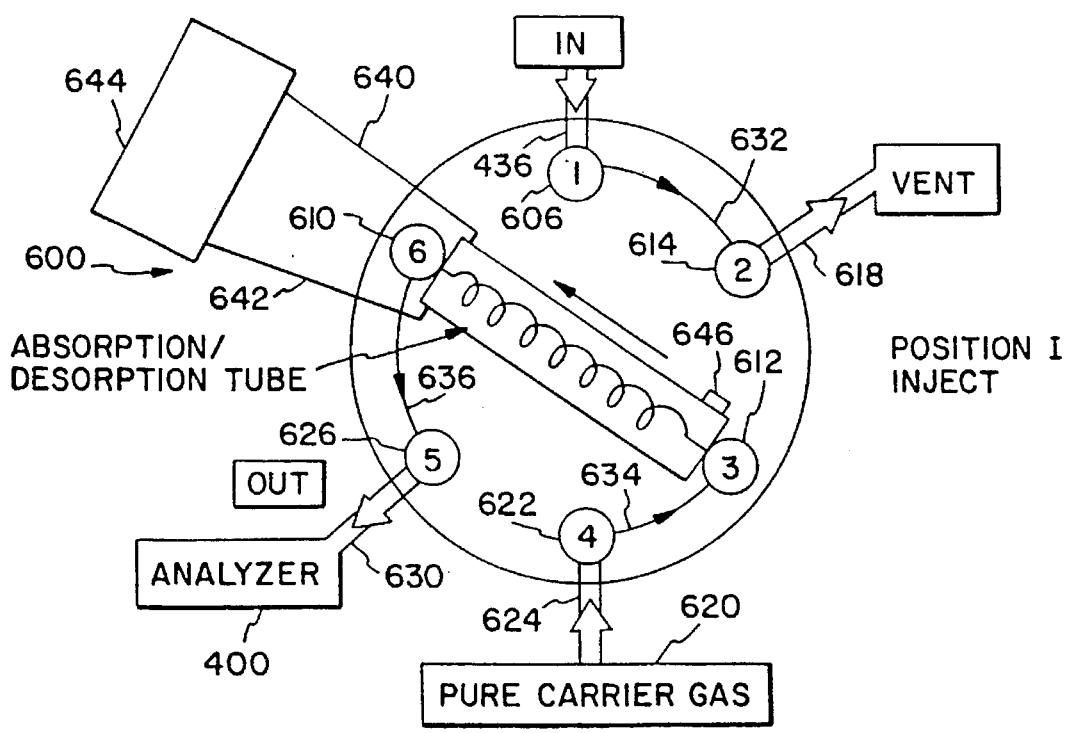
FIG. 13B is a diagrammatic representation of the six-port valve used in the present invention with the six-port valve in the inject position.

If a gas chromatograph/electron capture detector is utilized as the chemical analyzer 460, a six-port valve 600 is utilized as an interface between the vaporization chamber 416 and the chemical analyzer 460 as shown in FIG. 11C. In this embodiment, the vaporization process is identical to that previously described; however, the carrier gas sweeps the vaporized material into the six-port valve 600 instead of directly to the chemical analyzer 460 or through the three-way valve 438. The six-port valve is used to vent more volatile and less volatile vapors from the vaporized sample, and to preferentially retain the vapor sample of interest for separation by the GC. This venting of unwanted vapors is desirable to avoid clogging the GC, or unduly extending the cycle time. FIGS. 13A and 13B illustrates the operation of the six-port valve and represent the two positions that the six-port valve 600 can occupy. The interface control unit, which is part of the control and data processing system, comprises a stepper motor, and is operable to switch the six-port valve 600 between the two positions. In either position, only pairs of ports are connected. In position 1, illustrated in FIG. 13B, ports 1 and 2, 3 and 4, and 5 and 6 are connected, and in position 2, illustrated in FIG. 13A, ports 2 and 3, 4 and 5, and 6 and 1 are connected. Position 2 places an adsorb-desorb tube 604 in the load position. The gas flow line 436 shown in FIG. 11B carries the gas containing the vaporized target materials and some possible contaminants into port 1 indicated at 606 in FIG. 13A of valve 600 wherein the gas automatically flows through an internal passageway 608 to port 6, indicated at 610 in FIG. 13A. Connected between port 6 and port 3 is the external adsorption/desorption tube 604 in which the gas containing the target material and some minor contaminants pass through. The adsorbing material inside the tube 604 is specifically targeted for the target molecules in vapor form; therefore, the carrier gas and the contaminants flow through the tube 604 to port 3, indicated at 612 while the target material is adsorbed within the tube 604. The carrier gas and contaminants flow from port 3 indicated at 612 in FIG. 13A to port 2 indicated at 614 in FIG. 13A through internal passageway 616, and is vented to the external atmosphere through exhaust line 618. Pure carrier gas supplied from a second gas supply means 620 is fed into port 4 indicated at 622 via line 624. The pure carrier gas automatically flows from port 4 indicated at 622 to port 5 indicated at 626 via internal passageway 628. The carrier gas then flows from port 5, indicated at 626 to the chemical analyzers 460 via line 630. The chemical analyzer 460, which includes a gas chromatograph, requires a continuous gas flow to remain operational. The use of the six-port valve 600 allows pure carrier gas to be fed continuously to the chemical analyzer 460, even when the adsorb/desorb tube 604 is in the adsorb cycle.

At the end of the adsorption cycle, the interface control unit of the control and data processing system then automatically switches the six-port valve 600 into position 1 which is the desorb mode as shown in FIG. 13B. Port 1, indicated at 606 in FIG. 13B still receives gas from the gas supply means 434 via line 436; however, the gas flows from port 1, indicated at 606 to port 2, indicated at 614 via internal passageway 632 and is vented to the atmosphere via exhaust line 618. Port 4, indicated at 622 is injected with pure carrier gas from supply 620 via line 624 which flows to port 3, indicated at 612 via internal passageway 634. As stated before, port 3, indicated at 612 and port 6, indicated at 610 are connected via an external adsorption/desorption tube 604; however, in this position, the carrier gas is flowing through the tube 604 in the opposite direction. Therefore, when the tube 604 is heated to desorption temperature, the gas will sweep the desorbed target material and carry it to port 6, indicated at 610, essentially free of contaminants. From port 6, indicated at 610, the target material flows to port 5, indicated at 626, via internal passageway 636 and to the chemical analyzer 460 via line 630.

The external adsorption/desorption tube 604 is electrically insulated from the valve body and contains a selected quantity of the adsorbing material which has the best characteristics for adsorbing the vaporized target material. High current connections are made to the ends of this tube 604 and are shown in FIGS. 13A and 13B as electric lines 640 and 642. Lines 640 and 642 are connected to the other end to a controlled current source 644. The controlled current source 644 is controlled by the interface control unit. A thermocouple 646 is shown attached to tube 604 in FIGS. 13A and 13B. This thermocouple 646 as stated previously, is used to monitor the rise in the temperature of the tube 604 so as to achieve the proper temperatures for desorption. The gas sample which contains the target material, contaminants and excess gas, passes through the tube 604 and because it is cold, and the adsorber material has been selected to be a strong adsorber for the target material, most of the sample will be adsorbed at the end of the tube 604 near port 6. The contaminants are less strongly adsorbed and thus any adsorption of them will be throughout the length of the tube 604. Also, because the contaminants are not strongly adsorbed a larger portion of them will pass through the tube to the exhaust vent 618 and be discarded.

A desirable property of thermal desorption of gases or vapors on solid or liquid substrates is that the process can be highly thermally sensitive and thermally dependent. At a specified temperature the amount of any material desorbed is related to its physical and chemical properties and the physical and chemical properties of the adsorbing material. It is possible to choose adsorbing materials such that the contaminating materials are desorbed at a workable lower temperature than the target materials.

Careful thermal programming allows one to use these properties. An example is to heat the desorber tube 604 in a controlled fashion with the six-port valve 600 in position 2. The contaminants such as water vapor etc. are not strongly adsorbed and a low temperature will cause a major portion of them to leave the adsorber and pass out of the system through the vent. At the same time, the target materials will not be desorbed and will remain at the end of the adsorber tube 604 adjacent port 6. If the position of the rotor in the six-port 600 valve is now changed to position 1, two important changes are made. The adsorber tube 604 is now connected to the next stage in the sequence and the pure carrier gas flows through the adsorber tube 604 in the opposite direction to the previous gas flow direction. A rapid controlled increase in temperature will now cause the sample to be desorbed in a short period of time. This results in a sample which has been purified by the previously described adsorption and desorption process passing to the next stage in the process, contained in the minimum of pure carrier gas. Thus the sample has been twice purified of contaminants and concentrated in a much reduced volume of pure inert carrier gas.

During the vaporization process, and as illustrated in FIG. 11c, filter element 426a is in the vaporization chamber 416, filter element 426c is in the collection chamber 414 collecting the next sample of particulate matter, and filter element 426b is in the cleaning chamber 41B. Upon completion of this second sampling period the solenoid 430 is actuated by the PCAD actuator control unit of the control and data processing system thereby causing lever mechanism 432 to separate the first and second fixed SCAV plates 420 and 422. Once the separation of the first and second fixed SCAV plates 420 and 422 is completed, the stepper motor 428 is engaged by the PCAD actuator unit of the control and data processing system and rotates the circular plate 412 120 degrees, placing filter element 426a inside the cleaning chamber 418, filter element 426b into the collection chamber 414 and filter element 426c, with trapped particulates, in the vaporization chamber 416.

The cleaning chamber 418 is a sealed chamber similar to the vaporization chamber 416. In this chamber 418, a second pair of electrical terminals 415 are connected to filter element 426a when that particular filter element occupies the cleaning chamber 418. The second pair of electrical terminals 415 are connected to each of the filter elements 426a, b and c when each of them occupies this particular chamber 418. This second pair of electrical terminals 415 provides a computer controlled current to generate a specific amount of ohmic heat energy to vaporize any remaining particulate matter remaining on the filter element 426a. A cleaning suction fan 450, located in the second sample collection and analysis subsystem 500, draws any remaining vaporized material from the filter element 426a and the collection chamber 418 and vents it to the ambient environment. The cleaning suction fan 450 is connected to the cleaning chamber 418 via pipe 452. In one embodiment, pipe 451 is connected to both the cleaning chamber 418 and the flushing chamber 518 of the second sample collection and analysis subsystem 500. In this embodiment it is assumed that any vapors in the second sample collection and analytical subsystem 500 will pass directly through the filter element 426a in the cleaning chamber 418 and be vented to the ambient environment. In a second embodiment, pipe 454 branches off of main pipe 452 and thus provides a separate, parallel path for cleaning cycles. In this embodiment, a valve 453 is utilized to control the direction of the vacuum flow. Note that during the cleaning process, filter element 426b is inside the collection chamber 414 collecting the next sample, and filter element 426c is inside the vaporization chamber 416. This completes one 360 degree rotation and enables the process to start over again.

The SCAV 410 is designed in such a way that the movement of the circular plate 412 places filter elements 426a, b, and c in tightly sealed positions at each location so there is no contamination with the ambient air. The precise movement of the rotating circular plate 412 via the stepper motor 428 and the movement of the first and second fixed plates 420 and 422 are controlled by the PCAD actuator unit. The precise control of the three-way valve 438 and the six-port valve 600 as well as the gas flows are controlled by the interface control unit. Both the PCAD control unit and the interface control units are part of the control and data processing system which is described in detail subsequently.

Figure 14A:
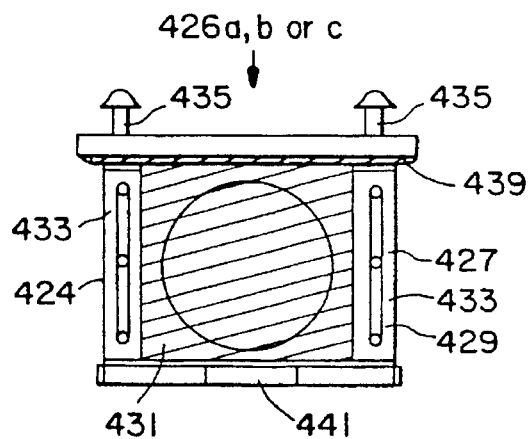
FIG. 14A is a diagrammatic representation of the top side of the filter elements utilized in the first sample collection and analysis subsystem of the present invention.

FIGS. 14a, b, and c illustrate the various views of the unique filter construction of the present invention. For purposes of illustration, the term sample filters or filter elements is construed to mean any of the three filter elements 426a, b or c. The sample filters are uniquely designed to enable the collection of sample particulates while facilitating the passage of vapor samples to the second sample collection and analysis system 500. They are also uniquely designed to facilitate vaporization of particulates and subsequent cleaning through pyrolysis and vacuuming.

Referring to FIG. 12, a rotatable plate with three removable filter elements is illustrated. The filter elements are inserted into the edge of rotating plate 412 with the hole in the filter element aligned with the hole of the filter unit as illustrated. Entrance to each filter cavity is from the circumference of the rotating circular plate 412. Each of the sample filter elements 426a, b, or c is uniquely designed to facilitate electrical current conduction, and as well as a gas tight fit while still providing for easy insertion and removal.

Figure 14C:
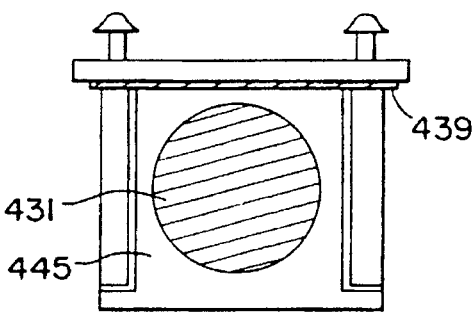
FIG. 14C is a diagrammatic representation of the bottom side of the filter elements utilized in the first sample collection and analysis subsystem of the present invention.
Figure 14B:
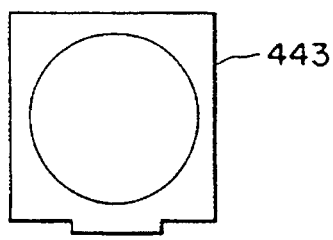
FIG. 14B is a diagrammatic representation of the top plane of the filter elements utilized in the first sample collection and analysis subsystem of the present invention.

As illustrated in FIG. 14a–c, the sample filter's frame 427 is constructed from anodized aluminum and then hard anodized. The hard anodized coating has been found to provide electrical insulation qualities which may be used in the design of the device. This also facilitates manufacturing, either by casting or machining. The frame 427 includes an electrical conductor 429 fitted at each end as indicated in the FIG. 14A. Each conductor 429 has a fitted piece or securing plate 433 which acts to hold a nickel or stainless steel mesh 431 in a firm electrical connection in place over the hole 412a, b, or c which may be circular, rectangular or square. The electrical conductors 429 extend through the frame 427 and end up as electrical terminals 435. In operation, when one of the filters 426a, b or c rotates into the vaporization cheer or the cleaning/purging chamber, the electrical terminals 435 engage commutator contacts which are provided for each of the chambers. FIG. 12 illustrates the contact points located on the commutator. The contact points 900 and 902 are for the cleaning cheer and contact points 904 and 906 are for the vaporization chamber. As is shown in the figure, the contact points 900–906 provide for spring loaded direct electrical contact in the direction of rotation. When process control initiates flash heating, an electrical current is passed to each of the terminals 435. The circuit between conductor 429 is completed by the stainless steel or nickel mesh screen which is ohmically heated by the current passing therethrough.

The frame 427 has a lip which fits against a planar portion formed in the circumference of the rotating circular plane 412. On the lip is a groove which holds a viton or other appropriate O-ring 439 in place so that when inserted into the cavity it makes a gas tight fit when snugged into place by a holding pin (not shown). The holding pin is braced against the top and bottom edges of the circumference of the rotating circular plane 412 by insertion into securing notches so that turning a single screw secures and seals the sample filter in place. Removal of the filter is easily accomplished by unscrewing the screw on the holding pin and removing it from the securing notches. A special tool is then sprung into slots at the protruding ends of the electrical terminals 435 and the sample filter is pulled from the cavity. FIG. 14B illustrates a top plate 443 which fits over the top side of the filter element 426a, b, or c shown in FIG. 14A. FIG. 14C illustrates the under side of filter element 426a, b, or c.

It is important to note that it is possible to replace the three filter SCAV 410 with a two filter SCAV 410 or even a single filter SCAV 410. In a two filter embodiment, there would be no cleaning chamber 418. The SCAV 410 would only have a collection chamber 412 and a vaporization chamber 414 for a continuous two step process per sampling period. In a single filter element embodiment, either one chamber suffices for the sampling and vaporization processes, or the single filter element is rotated or reciprocated between the two positions.

SECOND SAMPLE COLLECTION AND ANALYTICAL SUBSYSTEM

The second sample collection and analysis subsystem 500, shown in FIG. 11B, is the vapor collector and detector. It is located in line between the first sample collection and analysis subsystem 400 and the main suction fan 404 and the cleaning suction fan 450. The VCAD 500 is comprised of a sample collector and preconcentrator 510, SCAP, and the second chemical analyzer 560 which in the preferred embodiment is a gas chromatograph/electron capture detector, GC/ECD. In a second embodiment, the chemical analyzer 560 is an ion mobility spectrometer, or combination gas chromatograph/electron capture detector and ion mobility spectrometer. The VCAD 500 is used to collect, concentrate and analyze an sample volume of air for the targeted molecular vapor. This is accomplished by first selectively collecting and concentrating the molecular vapor in the SCAP 510 and then submitting the vapors to the second chemical analyzer(s) 560 for analysis. A description of the SCAP 510 operating in conjunction with both types of second chemical analyzers 560 is given in the following paragraphs.

SAMPLE COLLECTOR AND PRECONCENTRATOR (SCAP)

The SCAP 510 is used as part of the overall system to enhance overall system sensitivity and selectivity. In general terms, the SCAP 510 must simply discard, in a multi-step process, non-required molecules of air while not losing the targeted molecules of interest. In the sample collection and preconcentration step, the targeted materials are adsorbed onto a selected substrate, and then selectively desorbed into a smaller and more concentrated volume for analysis.

The SCAP 510 is used to collect and concentrate vapor samples from the air stream as it moves from one of the three sampling means through the SCAV 410 and onto the SCAP 510. The SCAP 510 is supplied with sample volume of the air by pipe 402 which extends from the SCAV 410 to the SCAP 510. During a sampling period, the high suction fan 404 draws the sample volume of air from one of the three sampling means thereby causing the air stream to flow into the SCAV 410. The filter elements in the SCAV 410 are designed to only physically trap certain target materials and allow the vapers to continue onto the SCAP 510. The vapors easily pass through the SCAV 410 and end up in the SCAP 510 where they will be physically trapped or adsorbed.

The SCAP 510 comprises a rotating circular plate. 512, a sampling chamber 514, a desorption chamber 516, and a flushing chamber 518. The sampling, desorption, and flushing chambers 514, 516, and 518 are formed from the union of first and second fixed SCAP plates 520 and 522. The first and second fixed SCAP plates 520 and 522 each comprise approximately one half of the volume of the three chambers 514, 516, and 518. The desorption chamber 516 is of slightly different design and is more fully described in subsequent paragraphs. The first and second SCAP fixed plates 520 and 522 are aligned such that the sampling chamber 514, the desorption chamber 516, and the flushing chamber 518 are configured 120 degrees apart from each other. The rotating circular plane 512 is disposed between the first and second fixed SCAP plates 520 and 522 and is capable of rotation therebetween. The rotating circular plane 512 has three circular holes 512a, b, and c equally spaced 120 degrees apart and covered with three mesh filter elements 526a, b, and c. The configuration of the three filter elements 526a, b and c on the rotating circular plane 512 is the same as that of rotating circular plane 412 utilized in the SCAV 410 and shown in FIG. 12. The rotating circular plane 512, which is actuated by a motor 528, is rotated 120 degrees every sampling period so that each of the mesh filter elements 526a, b, and c occupies either the sampling chamber 514, the desorption chamber 516 or the flushing chamber 518 during a sampling period. The motor 528 utilized to rotate the rotating circular plane 512 is a stepper motor which is controlled by the VCAD actuator unit which is an integral part of the control and data processing system. On completion of each rotation, a lever mechanism 532, which is actuated by a solenoid 530, pulls the first and second fixed plates 520 and 522 together so that each of the three filter elements 526a, b, and c are sealed in either of the three chambers 514, 516, and 518 during a particular sampling period. The solenoid 530 and the lever mechanism 532 are controlled by the VCAD actuator unit. The three filter elements 526a, b, and c are completely sealed in an air tight fashion in each of the three chambers 514, 516, and 518. The air tight seal is accomplished by the force supplied by the lever mechanism 532 and because each of the three chambers 514, 516, and 518 contain an O-ring seal. The O-ring seals are placed around the perimeter of the chambers, or more accurately, the half chambers in each of the first and second fixed plates 520 and 522. To completely illustrate the design and operation of the SCAP 510, a complete 360 degree rotation of the rotating circular plane 512 is described.

To illustrate the three sampling periods which corresponds to one 360 degree rotation of the rotating circular plane 512, it is necessary to state or assume that filter element 526a is inside the sampling chamber 514, filter element 526b is inside the desorption chamber 516, and filter element 518 is inside the flushing chamber 518 at the system start-up time. In this position, the filter element 526a and hole 512a are directly in line with pipe 402 and thus filter element 526a is capable of selectively collecting target vapor molecules which may be drawn from any of the three sampling means during a sampling period. A complete description of the filter elements 526a, b, and c is given in subsequent paragraphs. Upon completion of the first sampling period, the solenoid 530 is actuated by the control and data processing system thereby causing lever mechanism 532 to separate the first and second fixed SCAP plates 520 and 522. Once the separation of the first and second fixed SCAP plates 520 and 522 is completed, the stepper motor 528 is engaged by the control and data processing system and rotates the circular plane 512 120 degrees placing filter element 526a, with adsorbed vapors, inside the desorption chamber 516 while filter element 526b is placed in the cleaning chamber 518 and filter element 526c is placed inside the sampling chamber 514.

The desorption chamber 516 is a sealed chamber comprising a gas heating element (not shown) which is connected to a power source of the control and data processing system. An external carrier gas flow from gas supply 534 and carried by pipe 536 enters the desorption chamber 516 through a fitting 517 in the second fixed SCAP plate 522. The gas flow passes over the gas heating element where it is heated to a predetermined level to cause desorption of the targeted material from the adsorbates as it passes over and through them. In the preferred embodiment, the gas utilized is an inert gas; however, other less non-reactive gases can be utilized. It has been found through experimentation that the heating element may be a stainless steel screen fitted in a hard anodized aluminum frame, or a tungstem or wire wound ceramic frame. The fitting 521 on the first fixed SCAP plate 520 is designed to gather the carrier gas with vapor sample in as small an area as possible to enhance concentration of the sample as well as to maintain a fixed heat in a thermally insulated manner so, as to minimize the transfer of heat to the body of the desorption chamber 516. In the preferred embodiment, fitting 521 is conically shaped and insulated from the first fixed plate 520 by the insertion of a ceramic bushing. The fitting 521 is maintained at a predetermined temperature to facilitate the free passage of the sample in the carrier gas to the next preconcentration stage without adsorption on the wall of the fitting 521. The carrier gas, once it has reached the desired temperature, sweeps the desorbed material from the desorption chamber 516 via line 519 into the next concentrator stage.

Figure 11E:
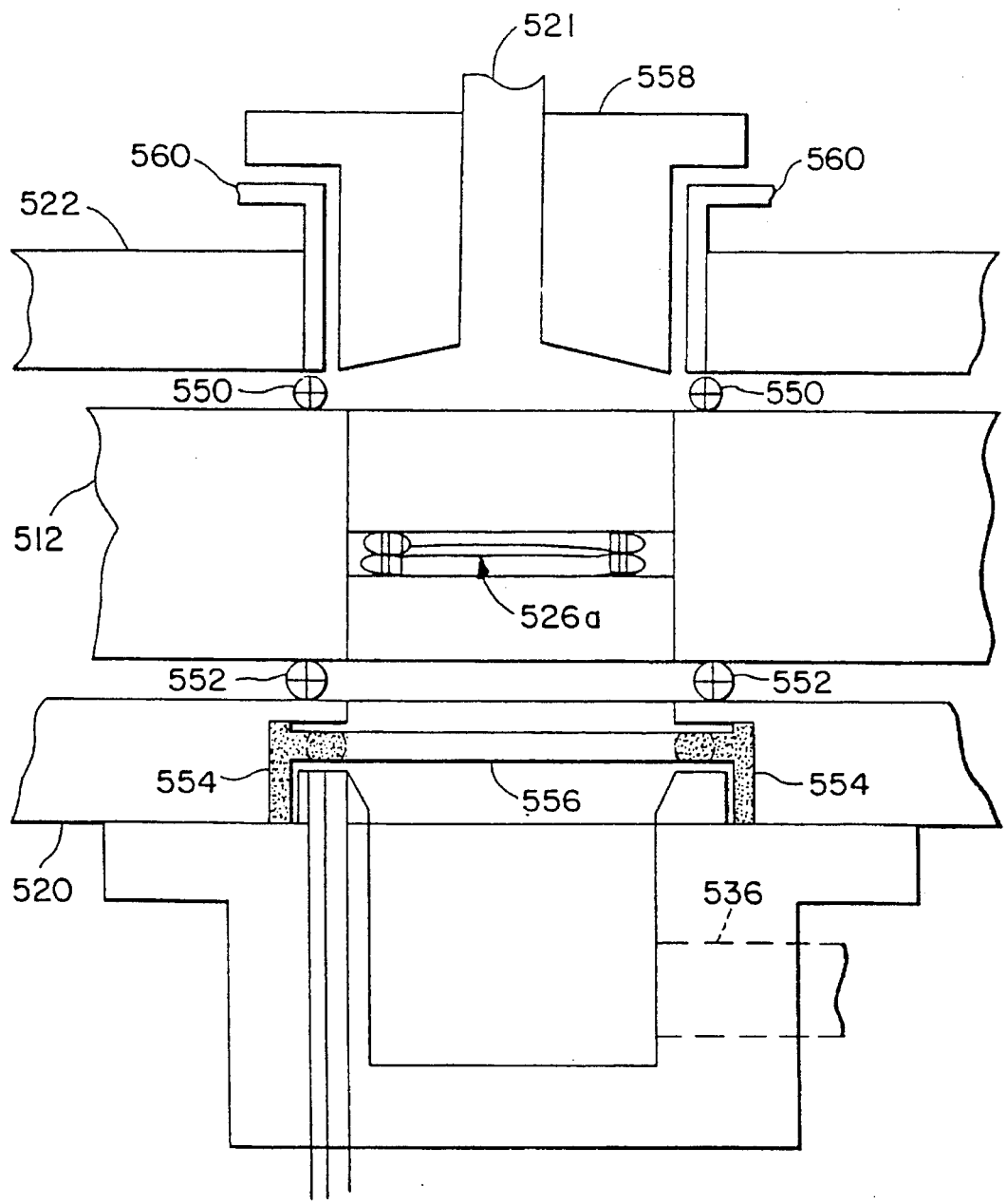
FIG. 11E is a diagrammatic representation of the desorption chamber of the present invention.

Referring the FIG. 11E, there is shown a more detailed diagram of the desorption chamber 516. The rotating circular plate 512 with filter element 526a is positioned between the first fixed plate 520 and the second fixed plate 522. Two O-ring seals 550 and 552 are shown between the first fixed plate 520 and the rotating circular plate 512 and between the rotating circular plate 512 and the second fixed plate 522. A ceramic heating screen holder 554 is shown holding heating element 556. The carrier gas enters the chamber 516 through gas line 536 and travels upward over the heating element 556 where it is heated to a temperature high enough to desorb any vapors on filter element 526a. The upper half of the chamber 516 is of smaller volume. As is shown in the figure, the upper half is conically shaped. The upper half has a stainless steel jacket 558 and a ceramic bushing 560 for insulation. The concentrated sample exists for the desorption chamber 516 through fitting 521 which is part of steel jacket 558.

The secondary preconcentrator 538 is a six-port valve identical to the one utilized in the first sample collection and analysis system. The concentrated sample from the desorption chamber 516 is swept into the six-port valve 538 along with some unwanted materials via the carrier gas flow. The pipe 519 is heated to a certain extent to prevent the possible absorption of the vapors onto the wall of the pipe 519. Once inside the six-port valve 538, the sample either passes through a sample loop to either a vent to the ambient environment or to the chemical analyzer 560 depending upon the position of the six-port valve 538. The sample loop is the desorption tube 604 shown in FIGS. 13A and 13B. The operation of the six-port valve 538 is identical to the operation of the six-port valve 600 utilized by the first sample collection and analysis subsystem 400.

In a slight variation of the previously described process, it has been found that a further purification of the sample volume can be effected by venting unwanted material to the ambient atmosphere through manipulating the route and timing of the carrier gas flow so that a purer sample of the target material is fed to the chemical analyzer 560. Normally the six-port valve 538 is positioned so that it is supplying pure gas to the chemical analyzer 560 from a gas supply like gas supply 620 in FIGS. 13A and 13B and receiving carrier gas and sample from the desorption chamber 516 and passing it through the sample loop then back to the six-port valve 538 and out to the ambient environment. The more volatile vapors containing the unwanted materials are desorbed first in the desorption process carried on in the desorption chamber and are the first to arrive at the six-port valve 538. The time of positioning the six-port valve 538 so that it transfers the vapor in the sample loop is such that the unwanted lighter vapors have already passed through the sample loop and have been vented before the sample is fed into the chemical analyzer 560.

During the desorption process wherein filter element 526a is in the desorption chamber 516, filter element 526b is in the cleaning chamber 518, and filter element 526c is in the sampling chamber 514 collecting the next sample of vapor. Upon completion of the second sampling period, the solenoid 530 is actuated by the control and data processing system thereby causing lever mechanism 532 to separate the first and second fixed plates 520 and 522, and upon completion of the separation of the first and second fixed plates 520 and 522, the stepper motor 528 is engaged by the control and data processing system and rotates the circular plane 512 120 degrees placing filter element 526a inside the cleaning chamber 518, filter element 526b into the sampling chamber 514 and filter element 526c, with adsorbed vapors, into the desorption chamber 516.

The concentrated sample volume is swept from the desorption chamber 516 or the six-port valve 538 into a gas chromatograph/electron capture detector combination. The process of gas chromatography consists of separations of vaporized components by a combination of partition chromatography, varied degrees of adsorption chromatography, and the varied relative volatility of the vaporized components. The concentrated sample volume containing compounds of interest are swept into a long gas chromatograph column which is coiled in a constant high-temperature compartment. The column is packed with inert, organic solid supports coated with one or more non-volatile organic coatings. The support with its organic coating constitutes the stationary phase of gas liquid partition chromatographic systems. As the volatized components pass through the column they partition between the stationary phase material in the column and the volatile phase, which is a stream of inert carrier gas. This partitioning reflects the relative volatility of the vaporized components. Compounds exhibiting lower volatility have less affinity for the stationary phase and accordingly exit the gas chromatograph first. The concentrated vapor sample exits the gas chromatograph as a continuous stream with varying volatility compounds separated spatially. This continuous stream then enters the electron capture detector.

The electron capture detector is a device utilized to measure the concentration of electron-capturing chemical species in the effluent from a gas chromatographic column. The ECD is insensitive to amines, alcohols and hydrocarbons, but very sensitive to halogens, anhydrides, peroxides, ketenes and nitro groups and thus particularly lends itself to this particular application. The electron capture detector is a gas ionization chamber within which conduction electrons are produced at a known rate, typically by a radioactive source, and captured by the electro-negative species within the sample of output from the gas chromatograph. Electrical measurements made at the chambers electrodes are made to determine the free electron density and then determine the concentration of electron capturing compounds. The electrical measurements result in a pulse train whose frequency is linearly related to the concentration of the compounds present in the sample.

The computer of the control and data processing system, to be described in a subsequent section, is preprogrammed to detect certain signature molecules, which are also discussed in subsequent sections. The time of travel from initial injection through capture by the electron capture detector is determined by the particular compound. Through experimentation, it has been determined that the time of travel of the signature molecules for dynamite and nitroglycerine began at approximately 1.5 seconds and end at 2.5 seconds, with a peak at approximately two seconds. Therefore, the computer will open a 25 ms window at two seconds to determine if any signature molecules are present. In addition, since the pulse train's frequency varies with the concentration of the various compounds, the concentration of the particular signature molecules for dynamite and nitroglycerine may also be determined by logging the frequency of the resultant pulse train.

The cleaning chamber 518 is a sealed chamber similar to the desorption chamber 516. It provides for a thermal cleansing of any vapors or particulates which may remain after the desorption process. When filter element 526a or any filter element 526a, b, or c is in the cleaning chamber 518, a pure gas flow from gas supply means 534 is routed to the filter element 526a over a second heating element not shown. A computer controlled current generates heat energy to desorb any remaining vapor and particulates from the filter element 526a. The gas flow is used to sweep the desorbed material through a fitting 523 and into pipe 452 which is connected to the vacuum cleaning fan 450 which draws the debris from the cleaning chamber and vents it to the ambient environment. During the cleaning process, filter element 526b is inside the sampling chamber 514 collecting the next sample, and filter element 526c is inside the desorption chamber 516.

The SCAP 510 is designed in such a way that the movement of the rotating circular plane 512 places filter elements 526a, b, and c in tightly sealed positions at each location so there is no contamination with the ambient air. The precise movement of the rotating circular plane 512 via the stepper motor 528 and the movement of the first and second fixed SCAP plates 520 and 522 are controlled by the VCAD actuator unit. The precise control of the six-port valve as well as all the gas flows are controlled by the interface control unit. Both the VCAD control unit and the interface control units are part of the control and data processing system which is described in detail subsequently.

Figure 15A:
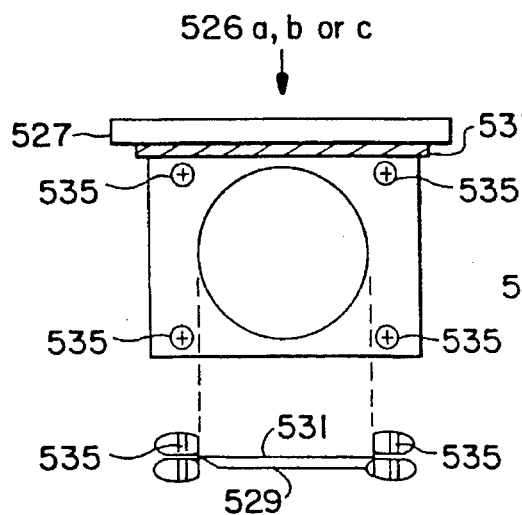
FIG. 15A is a diagrammatic representation of the top side of the filter elements utilized in the second sample collection and analysis subsystem of the present invention.

Referring to FIG. 15A and B, there is shown two views of the unique filter element design for the SCAP 510. For purposes of illustration, the term sample filters or filter elements is construed to means any of the three filter elements 526a, b, or c. The sample filters 526a, b, and c each consist of a frame 527 which holds two stainless steel screens 529 and 531 such that a cavity is formed between them. The cavity is filled with a measured amount of adsorbent material with an affinity to adsorb molecules of the target materials. The two filter screens 529 and 531 are held in place by a plate 533 which fits onto the frame 527 and is secured by four bolts 535. The frame 527 has a lip on which is fitted an O-ring seal 537 to provide a sealed surface when the filters 526a, b, or c are inserted into the cavities located on the rotating circular plane 512.

The sample filters frame 527 is constructed from aluminum which is then hard anodized. This has been found to provide the inert surface and thermal qualities required in this type of work. Normally a material such as stainless steel, nickel or a ceramic material such as Maycor would be used to achieve these ends. Through experiment it has been found that the hard anodized aluminum may be used. This facilitates manufacture either by casting or machining.

The adsorbent material used in the various stages of concentration of the target materials may be selected from a vast group of materials commonly used for vapor sampling including Tenax and Carbotrap. There are other adsorbing materials that can be used with the present invention depending on the particular materials that are to be detected and isolated.

The three filter SCAP 510 can be replaced with a two filter SCAP 510 or a single filter SCAP 510. In the two filter embodiment, there would be no cleaning chamber 518. The SCAP 510 would only have a sampling chamber 512 and a desorption chamber 514 for a continuous two step process per sampling period. In a single filter element embodiment, either one chamber suffices for the sampling and desorption processes, or the single filter is switched between the two positions.

ANALYSIS

The analysis of the purified target material consists of identifying the materials and determining the amounts present. Because the original concentrations were so low with respect to many other common ambient materials it is possible for there to be, even under the best of purification and concentration systems, some remaining impurities of materials with similar characteristics to the target materials. Thus the analysis system must be capable of separating the target material response from the response due to interfering materials.

Two forms of analysis systems are used either separately or in combination in both the first and second sample collection and analysis subsystems 400 and 500. The first sample collection and analysis subsystem 400 utilizes an ion mobility spectrometer, a gas chromatograph/electron capture detector, or both. The final detector for the gas chromatograph is usually an electron capture detector, however the ion mobility spectrometer can also be used as the second detector if desired. Depending on the application, a photo ionization detector or a nitrogen-phosphorus detector or some other detector may be also used following the gas chromatograph. The gas chromatograph may be of the "packed column" type or the capillary column type. If both a gas chromatograph/electron capture detector and ion mobility spectrometer are utilized, they can be used separately or in a combined fashion. A valve can be utilized to direct the collected and purified sample to either or both of the analyzers. The second sample collection and analysis subsystem 500 also utilizes a gas chromatograph/electron capture detector and/or an ion mobility analyzer. The first and second sample collection and analysis subsystems 400 and 500 can be run simultaneously or separately and thus both sets of chemical analyzers can be run simultaneously or separately.

In the preferred embodiment, an ion mobility spectrometer is the analyzer 460 for the first sample collection and analysis subsystem 400. The first sample collection and analysis subsystem 400 is used to collect particulates and vaporize these particulates for chemical analysis. The particulates of interest are associated with plastique explosives such as C4, DM-12, and SEMTEX. As was stated previously, plastique explosives have extremely low vapor pressures ranging from 10,000 to 1,000,000 times less than that of conventional explosives such as dynamite, nitroglycerin, and trinitrotoluene. The analysis of these particulates is based upon the detection of certain signature molecules. For plastique explosives, these signature molecules are cyclotrimethylenetrinitramine, RDX, or pentaerythritol tetranitrate, PETN. The ion mobility spectrometer is set to detect these signature molecules by creating a sample window for each of them. A window is utilized as opposed to trying to develop a direct match because one cannot expect a pure sample of the signature molecule. If a particular compound analyzed fits into one of the above windows, the sample sampled is deemed to have been in contact with a plastique explosive.

In the preferred embodiment, a gas chromatograph/electron capture detector(s) is the analyzer 560 for the second sample collection and analysis subsystem 500. The second sample collection and analysis system 500 is used to collect vapors and concentrate them for chemical analysis. The vapors of interest are associated with the conventional explosives enumerated above. The analysis of these vapors is also based upon the detection of certain signature molecules. For dynamite, the signature molecule is ethylene glycol dinitrate or EGDN. For nitroglycerin, the signature molecule is nitroglycerin, or NG. For trinitrotoluene, or TNT, the signature molecule is dinitrotoluene or DNT. Like the ion mobility spectrometer, the gas chromatograph/electron capture detector(s) is set to detect these signature molecules by creating a sample window for each of them.

There are presently a variety of international groups including national security agencies, the military and international manufacturers of explosives, that are working or deciding on a particular agent to be added to all explosives so that they may be more readily detected. The particular tagent that is decided upon will become one of the signature molecules that will be searched for in the analysis phase of the explosive screening process. A list of the signature molecules currently tested for is given in Table 1 set forth below. The table indicates the name, code, formula and use of each compound. Explosives are typically categorized as primary, secondary, or high explosives and propellants in order of decreasing sensitivity to energy input. In other words a primary explosive is more sensitive to heat for example, than a secondary explosive.

Whatever analysis system is used the analysis must be completed in a time that is short enough that the free flow of people, luggage and baggage is not unduly inhibited. This also implies that the time for the concentration and purification process is short as well.

If all the valves in the system are motor driven or solenoid driven valves, the flow directions timings and magnitude may be controlled and varied. The time and temperature parameters are controlled and variable. Thus the physical characteristics of the complete system may be adjusted to detect a wide range of target materials and the sensitivities may be adjusted to accommodate a wide range of threats as perceived by the authorities using the system.

All the processes involved in the collection and concentration as well as the final analysis of the collected material is controlled by the computer of the control and data processing system and will by fully explained in the following section.

CONTROL AND DATA PROCESSING

The primary requirement for the control and data processing system of the screening system is that it reports the presence of, and if required, the level of specified substances. This means that the equipment must be configured and controlled to make the required measurement and it also means that the result must be presented to the user in a usable form. The subject or target materials may be present in varying amounts in the environment of the system and therefore, the system must be capable of distinguishing between this background level and an alarm level. It may also be a requirement to report on this background level.

A secondary requirement for the control and data processing system of the integrated system is self diagnostic, as there may be considerable time between alarms, the control and data processing system must be capable of performing confidence checks that are satisfactory to the operator on demand. There must also be routine self checks and calibration procedures performed on the total system by the control and data processing system. Basically, this ensures that the test results, whether positive or negative, are believable.

A third requirement for the control and data processing system is ease of reconfiguration and versatility. The range of target materials may be changed from time to time, and the system must be capable of varying its internal operation

TABLE 1

| Name | Code | Formula | Use |
|------|------|---------|-----|
| ethylene glycol dinitrate | EGDN | $O_2NOCH_2CH_2ONO_2$ | liquid explosive |
| nitroglycerin | NG | $H_2CONO_2$<br>$HCONO_2$<br>$H_2CONO_2$ | liquid secondary explosive ingredient in commercial explosives and propellants |
| 2,4,6-trinitrotoluene | TNT | $CH_3$<br>$O_2N \quad NO_2$<br>$NO_2$ | secondary high explosive |
| cyclotrimethylene trinitiramine | RDX | $NO_2$<br>$N$<br>$N \quad N$<br>$O_2N \quad NO_2$ | secondary high explosive used as a booster |
| pentaerythritol tetranitrate | PETN | $O_2NOCH_2 \quad CH_2ONO_2$<br>$C$<br>$O_2NOCH_2 \quad CH_2ONO_2$ | secondary high explosive used as a booster | parameters under program control to detect these materials. It is desirable that the rigor of the measurement in terms of time constraints and number and types of substances detected be alterable in an expeditious fashion at any time. The user's requirements in terms of level of threat and types of materials may quickly change and the equipment must respond to these changing needs.

The final requirement for the control and data processing system is that the parameters and operations of all of the sampling chambers and the first and second sample collection and analytical subsystems must be monitored and controlled. This means that all internal timings, temperatures and mechanical components must be controllable by the control and data processing system.

The primary method of achieving these requirements is to put the total system under the control of a stored program digital computer. This computer through a series of modularized software routines performs the data analysis and presents the results in the required form to the user. The computer through another series of modularized software routines continuously performs self diagnostic and self calibration procedures on the total system, and alerts the user to any potential problems. The computer through still another set of modularized software routines controls all the processes of the total system and shall be more fully explained in subsequent paragraphs.

One primary benefit of this system of control is reliability. By themselves the components are rugged and reliable and not prone to failure. However, any system made up of many items is subject to drifts due to ambient changes and time. By having all components under program control and by arranging for a known input to the system such as a controlled injection of target material or target stimulant, there can be a calibration and self-diagnostic program. The function of this program is to calibrate the entire system and determine and store the required time, and temperature parameters etc. If these parameters are not within specified limits for any reason, the program can alert the user. Guided by a service program the user response can range from immediate shutdown to scheduling service at a later date, to simply noting the circumstances. By use of a modem this information can be easily transmitted to anywhere in the world. The other aspect of reliability in a system of this type is that the user must know that the system is reliable. Hopefully there will be very long periods of time between actual alarm events. However, if there is a calibration and self diagnostic program and associated hardware for realistic sample injection, the user can generate, at anytime, an actual/simulated alarm event as a confidence check.

The second primary benefit of this system of control is versatility. It is advantageous for the system to have the capability of detecting a wide range of explosives, a range of controlled chemical agents, drugs, and narcotics etc. All these materials have differing physical and chemical properties. These properties give rise to a set of internal parameters for optimum detection. However these parameters will be less than optimum for some other materials. But, if these parameters are all controllable and easily changed such as by simply reading in or activating a different program in the computer memory, then the user can effectively change the system to meet what is considered to be the threat at that time without making any hardware changes.

Referring now to FIG. 16, there is shown a block diagram representation of the control and data processing system 700 and its associated peripheral elements. The digital computer 702 or processor is an AT type personal computer running at 10 MHz and has a standard video display terminal 704. The computer 702 is responsible for process control, data acquisition, data analysis and display of analysis results. In addition, as mentioned previously, the computer 702 also contains software routines for self diagnostic and self calibration procedures. The computer 702 receives power from the power distribution unit 706 as does the sampling chamber portal 100, the hand-held wand 200, the automated baggage/parcel sampling chamber 300, and the process control unit 708. The process and control unit 708 under the control of the computer 702 interfaces and provides the necessary signals to run the sampling actuator unit 710, the interface actuator unit 712, the PCAD actuator unit 714, and the VCAD actuator unit 716.

The process and control unit 708 is a standard interface unit between the computer 702 and the various actuators. The sampling actuator unit 710 controls or actuates all processes involved in the collection of the sample volumes of air from the sampling chamber portal 100, the hand-held wand 200, and the automated baggage/parcel sampling chamber 300. Under software control, the process control unit 708 outputs commands to the sampling actuator unit 710, to control the suction of air from the various sampling means, and the actuation of the rotating brushes. The interface actuator unit 712 comprises the stepper motors which control the operation of the six-port valves, and the gas supplier means utilized for sweeping the samples into the chemical analyzers. The stepper motors and the gas supply means are run under software control. The interface actuator unit 712 is utilized to rotate the six-port valves between the adsorb and desorb positions and regulate the various gas flows. The PCAD actuator unit 714 comprises a stepper motor for the rotation of the rotating circular plate, and provides the signal for control of the solenoid utilized to operate the lever mechanism which either joins or separates the first and second fixed plates. The VCAD actuator unit 716 comprises a stepper motor for the rotation of the second rotating circular plate, and provides for the control of the second solenoid utilized to operate the second lever mechanism which either joins or separates the second set of first and second fixed plates. Data from the chemical analyzers 460 and 560 is brought directly into the computer 702 for processing through a data acquisition plug in card. Data from the gas chromatograph/ECD system is taken into the computer 702 as a varying frequency, and data from the IMS system is taken into the computer 702 as a varying analog voltage. The data input to the control and data processing system 700 is correlated by processor 702 to the process control module 708 which generates the necessary interrupts for processor 702 so the data can be input at the proper time intervals.

The computer 702 has an internal clock which provides the reference clock for all timing sequences. Therefore, because all the valves and mechanical motions are being actuated by the computer, all gas and sample flows in the equipment are controllable with respect to the time of actuation. The relative sequencing and timing of actuations are simply steps in a stored program in the memory of the computer. In addition, all the temperatures in the equipment are read into the computer and all heating functions are actuated by the computer. Therefore, all the temperatures and their magnitudes at any time and rate of change with respect to time are under program control. The data output from the chemical analyzers from both the first and second sample collection and analytical subsystems are processed as necessary and the required information is extracted and displayed by the same computer.

A unique feature of the present invention is that of the use of a correlation and detection system. In a high throughput environment, such as an airport, with overlapping sample acquisition and analyzer periods, there exists a need for a means to positively verify the individual or object sampled at the time the sample is taken, in the event the sample contains the target molecules. In the preferred embodiment, the analysis occurs approximately 12 seconds after the sample is taken, and in a fast moving stream of luggage or individuals, identification would be difficult if not impossible. Therefore, a video imaging camera, either motion or still is provided to record the image of the individual or luggage sampled. This image is then correlated with the results of the sample taken by computer 702. This video imaging means or image capturing means is placed in a location such that it can capture an image of whatever is in the sampling area being sampled. For example, the imaging means can be placed inside the sampling chamber portal 100, as illustrated by video camera 109 shown in FIG. 3, or at a convenient location to capture images(s) of luggage or other objects entering or exiting the automated baggage/parcel sampling chamber 300, and at a location convenient to capture images(s) of individuals or objects being sampled by the hand-held wand 200, shown in FIGS. 4 through 6.

The imaging means is placed in a location so as to capture an image of an individual or object being sampled by one of the various sampling means. The imaging means can be placed in close proximity to the sampling area or in a remote location where it can be more easily hidden if desired. Whatever type of imaging means is utilized, the captured image must be stored. The captured image is either stored on a video cassette recorder or a separate storage device. If the image is stored on a separate storage device, the video signal must be digitized by any type of standard digitizing circuit. Each stored image is given an identification code by the control and data processing system because of the delay between capturing an image and the analysis of the person or object sampled. If either or both of the first and second sample collection and analysis subsystems 400 and 500, shown in FIGS. 11A–11C, detect the presence of any of the target materials, then an alarm is set. The control and data processing system then requests the image associated with a particular stored image from either the video cassette recorder or the separate storage means by its identification number. The control and data processing system then correlates the particular stored image with the results of the chemical analysis. In normal operation the images are saved only until the analysis is completed. In the event of an alarm, the associated image is flagged to prevent erasure. In addition, the correlation and detection system comprises a video display so one can view the image to determine the identity of the object or individual who set off an alarm.

The computer program utilized to run the detection and screening system of the present invention includes the steps of defining target vapor and target particulate parameter windows, wherein each window brackets the systems response to each of the selected molecules of interest that are indicative of a target material. The program also includes the steps of defining a sampling sequence having at least one sampling period, defining an actuation sequence, enabling system operation, acquiring data from the system, and then correlating or matching the acquired data with the parameters previously developed for the target vapors and target particulates. The program then enables a detection signal upon a match or correlation between the acquired data and the target parameters. In addition, the computer program correlates the acquired data with an image of the object or individual being screened, so that when there is a correlation between the acquired data and the target parameters, a positive identification of the object or individual can be made.

The step of defining target vapor and target particulate parameter windows includes loading the CPU memory attached to the chemical analyzers with the specific signature molecule profiles or signal patterns. The step of defining a sampling sequence includes initializing the parameters associated with the first and second sample collection and analysis subsystems. The step of defining the actuation sequence and the step of enabling system operation includes the sequencing of the various operations associated with the collection, vaporization, and desorption processes involved in the operation of the detection screening system, as hereinbefore previously described. The step of acquiring data and correlating the acquired data with the target vapor and target particulate parameters includes the step of performing the analysis, collecting the output data and comparing the collected data with the window parameters to determine if there is a match. When different detectors are used for the first and second subsystem, different profiles or signal patterns are-developed which are representative of that detector's response to a specific target molecule of interest.

Figure 17:
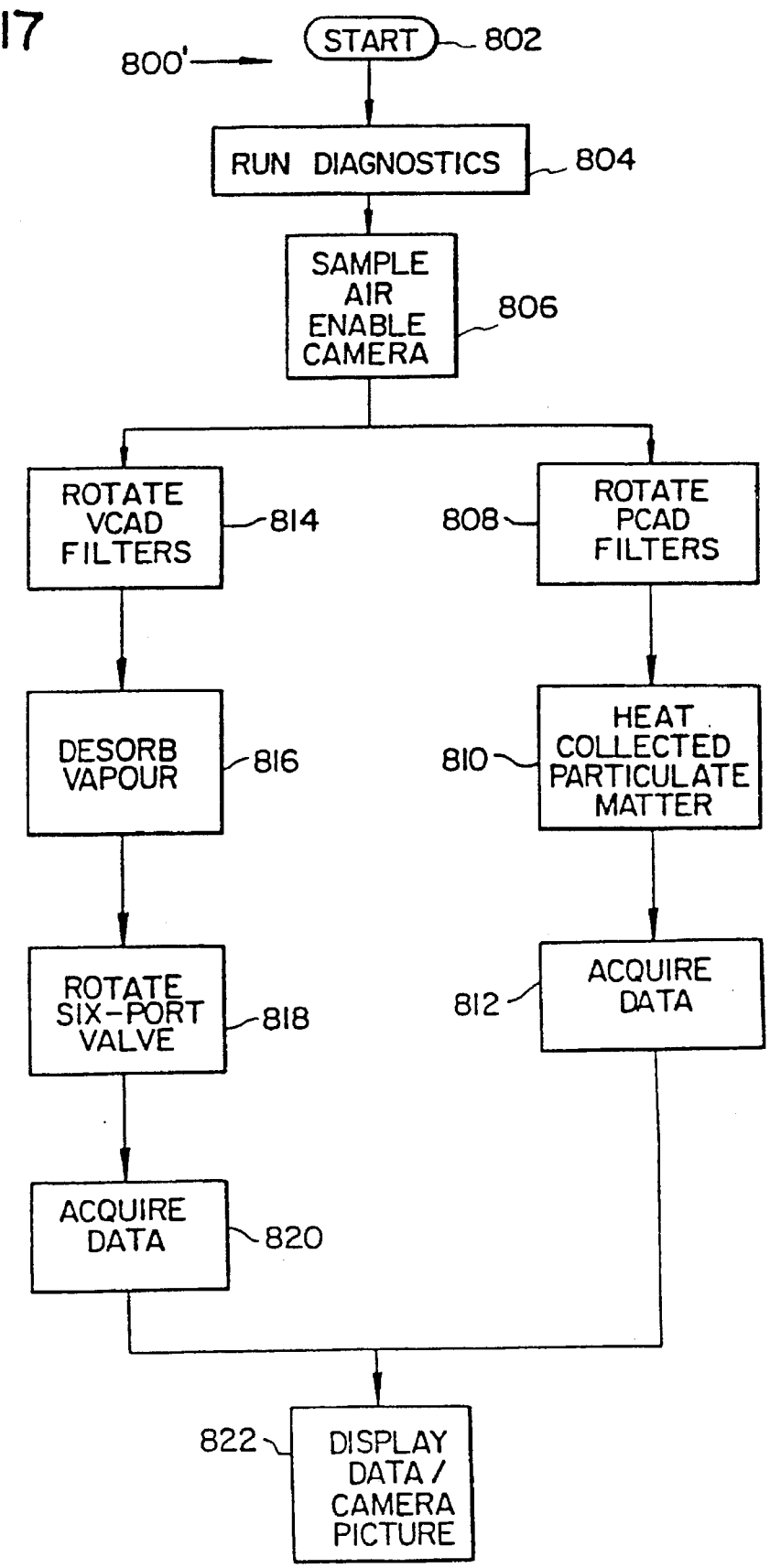
FIG. 17 is a flow chart of the software routine utilized to control the operation of the present invention.

FIG. 17 is a flow chart 800 showing the overall process control as accomplished by the control and data processing system and run by the digital computer 702. Block 802 of the flow chart 800 is simply the starting point or entry into the entire software package. The Run Diagnostics block 804 represents the block of software that is responsible for self diagnostic and self calibration. Basically, this block of software runs various programs for exercising various aspects of the detection and analysis routines. The Sample Air and Enable Camera block 806 represents the block of software that causes the air sample to be drawn from the portal, the hand-held wand or the automated baggage/parcel sampling chamber, and drawn into the first and second sample collection and analytical subsystems. This software controls the operation of the sampling actuator unit 710 shown in FIG. 16. The Sample Air and Enable Camera block 806 also represents the block of software responsible for enabling a camera to capture an image of the object or individual being sampled. The captured image is then correlated to the chemical analysis data associated with the sample drawn from the individual or object and is then saved in memory for an archival record to be used as an identification means. Typically, the images of an individual or object will be saved for the last three to six sampling periods, unless where one or more of the target materials has been detected. After the Sample Air and Enable Camera block 806, the flow chart 800 diverges into two paths that run simultaneously. One path represents the operation of the first sample collection and analytical subsystem while the second path represents the operation of the second sample collection and analytical subsystem.

Figure 15B:
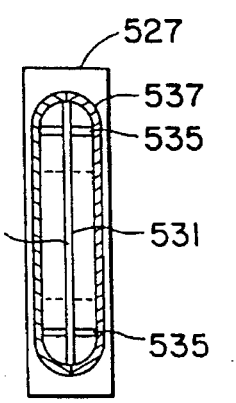
FIG. 15B is a diagrammatic representation of the side view of the filter elements utilized in the second sample collection and analysis subsystem of the present invention.

The first path in flow chart 800 is as follows: The Rotate PCAD Filters block 808 represents the block of software that is responsible for the rotation of the rotating circular plane and the union and separation of the first and second fixed plates. Basically, this block of software controls the PCAD actuator unit 714 shown in FIG. 15. The Heat Collected Particulate Matter block 810 represents the block of software that is responsible for the controlling of the vaporization process. This block of software controls the flash heating process as well as the gas flows utilized to inject the vaporized sample into the chemical analyzer. This block of software controls the interface actuator unit 712 shown in FIG. 16. The Acquire Data block 812 represents the block of software that is responsible for the acquisition of data from the chemical analyzer(s) and the subsequent analysis and preparation for display of the resultant data. In addition, this block of software correlates the collected data with the image of the individual or objects captured by the camera means.

The second path in the flow chart 800 is as follows: The Rotate VCAD Filter block 814 represents the block of software that is responsible for the rotation of the second rotating circular plane and the union and separation of the second pair of first and second fixed plates. This block of software controls the VCAD actuator unit 716 shown in FIG. 16. The Desorb Vapor block 816 represents the block of software that is responsible for the controlling of the heating means and the flow of pure gas in the desorption process. The Rotate Six-Port Valve block 818 represents the block of software that is responsible for controlling the six-port valve utilized as the interface between the VCAD and the chemical analyzers of the VCAD so that the concentrated sample volume of air is properly routed to the analyzers. The Desorb Vapor block 816 and the Rotate Six-Port Valve block 818 both control the operation of the interface actuator unit 712 shown in FIG. 16. The Acquire Data block 820 represents the block of software that is responsible for the acquisition of data from the chemical analyzer(s) 560 and the subsequent analysis and preparation for display of the resultant data. In addition, this block of software correlates the collected data with the image of the individual or objects captured by the camera means.

Upon completion of the two Acquire Data blocks 812 and 820, the flow chart 800 is united once again. The Display Data/Camera Picture block 822 represents the block of software that is responsible for formatting the acquired chemical analysis data in a format that is readily displayed on a standard CRT and is easily understood. The captured image or picture can also be displayed utilizing standard display techniques. The entire software structure indicated in FIG. 17 is a cyclic process and following the step of block 822, returns to the Sample Air and Enable Camera block 806 and continues until stopped. The software further enables the system to run in a single cycle mode, a continuous cycle mode or a pause mode. As stated previously, the software routine is modularized and therefore can be easily changed, updated, removed or added on to.

Figure 18:
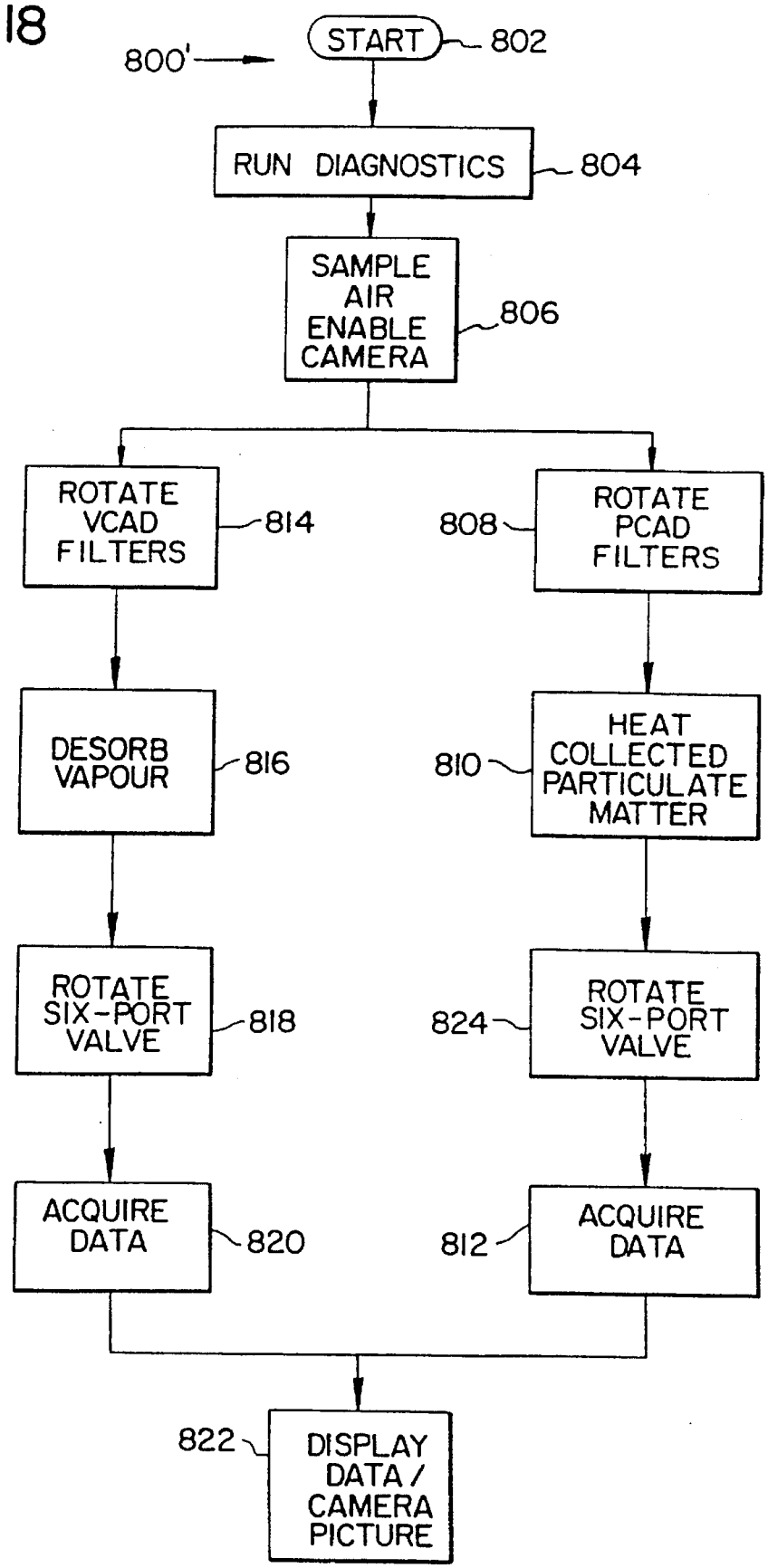
FIG. 18 is a flow chart of an alternate software routine utilized to control the operation of the present invention.

FIG. 18 is a flow chart 800' which shows an identical process as does the flow chart 800 in FIG. 17 with one exception. In flow chart 800', an additional Rotate Six-Port Valve block 824 is inserted between the Heat Collected Particulate Matter block 810 and the Acquire Data block 812. As before the Rotate Six-Port Valve block 824 represents the block of software that is responsible for controlling the six-port valve is utilized as an interface when a gas chromatograph analyzer is utilized.

There are basically three concepts that exist in the screening process. The first concept involves both the collection of vapors and particulates and their subsequent analysis. Therefore, the first concept utilizes both the first and second sample collection and analytical subsystems. The second concept involves only the collection of particulates and their subsequent analysis. Therefore, the second concept utilizes only the first sample collection and analytical subsystem. The third concept involves just the collection of vapors and their subsequent analysis. Therefore, the third concept utilizes only the second sample collection and analytical subsystem. The software is designed so that all three concepts for screening require approximately 11.0 seconds to complete whether run individually or simultaneously. An initial delay is added to the PCAD cycle so that the analysis of the PCAD system is completed at the same point in time that the analysis of the PCAD system is completed. This prevents confusion of test results when the system is run in continuous mode. When run in continuous mode, there is an overlap between the end of one screening cycle and the beginning of a second screening cycle, with each of the next screening cycles being completed each seven seconds. This overlap occurs between the analysis and display period of one screening cycle and the sample air through vaporize/desorb periods of a second cycle. This overlap requires that the software tasks in the screening process be run in a multi-tasking environment. .In a multi-tasking environment, the software routines are run in a foreground/background scenario in a true interrupt mode. The mechanical operations under software control are run in background while the analysis and data processing functions are run in foreground. The flow charts of FIGS. 17 and 18 are general representations of the software and should not be construed as timing diagrams. Table 2 given below illustrates the required steps associated times involved in the screening procedure utilizing this multi-tasking environment.

TABLE 2

| STEP | PCAD | VCAD |
| --- | --- | --- |
| SAMPLE AIR | 2.0 | 2.0 |
| ROTATE FILTERS | 1.0 | 1.0 |
| VAPORIZE/DESORB | 0.25–0.5 | 2.0 |
| INJECTION | 0.25–0.5 | 1.0 |
| ANALYSIS AND DISPLAY | 1.0 AND 0.75 | 5.0 |

It is important to note that the times given in Table 2 reflect the absolute times for each of the processes and do not reflect the total time for one sampling cycle. FIG. 19 is a sequence/timing diagram which better illustrates the various time parameters for each process in a sampling cycle or period. From 0.0 to 2.0 seconds, a sample volume of air is collected from either the sampling chamber portal, the hand-held wand or the automated baggage/parcel. sampling chamber. From 2.0 seconds to 3.0 seconds, the filters are rotated carrying the collected materials to the next stage of processing. From 3.0 to 5.0 seconds, the VCAD is concentrating the vapors collected. During this time period, the PCAD is idle. The vaporization and injection the collected particulates collected is accomplished from 6.0 to 6.25–6.50 seconds. From 5.0 to 6.0 seconds the concentrated vapors from the VCAD are injected into the chemical analyzers. From 6.0 to 11.0 second the analysis and display of the VCAD sample is accomplished. From 8.0 to 9.0 seconds the analysis of the PCAD sample is accomplished and from 10.25 to 11.0 seconds the display of the PCAD sample is accomplished. Therefore, both PCAD and VCAD operations are completed simultaneously. A second cycle or sampling period is shown starting at 7.0 seconds. The second cycle is identical to the first.

Although shown and described in what is believed to be the most practical and preferred embodiments, it is apparent that departures from specific methods and designs described and shown will suggest themselves to those skilled in the art and may be used without departing from the spirit and scope of the invention. The present invention is not restricted to the particular constructions described and illustrated, but should be constructed to cover of all modifications that may fall within the scope of the appended claims.

What is claimed is:

1. An automated sampling chamber with automatic baggage/parcel sampling means for obtaining an air sample having vapors or particulates entrained therein for use in a portable detection and screening system for detecting molecular vapor from a target material or particulates containing a target material on a baggage/parcel object, said target material including explosives, chemical agents, drugs or narcotics, said chamber comprising:
   (a) a plurality of sampling heads for gathering sample volumes of air, said sampling heads having rotating brushes for sweeping and collecting vapor from the environment surrounding the object and particulates attached to said object;
   (b) a means for automatically moving said object through said automated baggage/parcel sampling chamber;
   (c) an automated detection and screening system with a target material detector for collection and detection of any molecular vapors of a target material present in said sample volumes of air; and
   (d) a computer control system which controls the operation of said automated baggage/parcel sampling chamber and said detection and screening system.

2. The system of claim 1, wherein said automated baggage/parcel sampling chamber has a rectangular geometry with dimensions of six feet in length, thirty-eight inches in width, and thirty-two inches in height, said automated baggage/parcel sampling chamber adapted to fit over said means for automatically moving said object.

3. The system of claim 2, wherein said automated detection and screening system is a high duty cycle system having a plurality of reusable filter media which selectively collect particulates in a plurality of overlapping collection and detection cycles synchronized by said computer control system.

4. The system of claim 2, wherein said automated detection and screening system includes a first sample collection and analysis subsystem for collecting target particulates contained in said sample volume of air and converting said target particulates into a vapor sample for analysis.

5. The system of claim 2, wherein said means for automatically moving said object through said automated baggage/parcel sampling chamber is a conveyor belt.

6. An automated sampling chamber with automatic baggage/parcel sampling means for obtaining an air sample having vapors or particulates entrained therein for use in a portable detection and screening system for detecting molecular vapor from a target material or particulates containing a target material on a baggage/parcel object, said target material including explosives, chemical agents, drugs or narcotics, said chamber comprising
   (a) a plurality of sampling heads for gathering sample volumes of air, said plurality of sampling heads having brushes for sweeping and collecting vapor from the environment surrounding the object and particulates attached to said object, said plurality including:
      (i) a first sampling head located at an entrance end of said automated baggage/parcel sampling means which spatially extends the entire width of said sampling means, said first sampling head mounted in the base portion of said automatic baggage/parcel sampling means to sweep and draw vapors and particulates from the bottom of said object;
      (ii) a second sampling head connected to a roof of said automated baggage/parcel sampling means, said second sampling head adapted to sweep and draw vapors and particulates from the top of said object; and
      (iii) third and fourth sampling heads hinged to opposite sides of said automated baggage/parcel sampling means, said third and fourth sampling heads each adapted to sweep and draw vapors and particulates from the sides of said object.
   (b) a means for automatically moving said object through said automated baggage/parcel sampling chamber;
   (c) a control system which controls the operation of said automated baggage/parcel sampling chamber; and
   (d) a detection and screening system with a target material detector for collection and detection of any molecular vapors of a target material present in said sample volumes of air.

7. The system of claim 6, wherein said first sampling head is connected to a common plenum via a first valve where the common plenum leads to said target material detector.

8. The system of claim 7, wherein said second sampling head is mobile and connected to said common plenum via a second valve, said second sampling head having first sensor means for automatically, adjusting to the height of said object.

9. The system of claim 7, wherein said second sampling head comprises a first power head and rotating brush mechanism which moves over the top portion of said object in response to an output signal from said sensor means.

10. The system of claim 9, wherein said third and fourth sampling heads are mobile and connected to said common plenum through a third valve, said third and fourth sampling heads having second sensor means for adjusting to the width of said object.

11. The system of claim 10, wherein said third and fourth sampling heads comprise second and third power heads and rotating brush mechanisms which move over the sides of said object from one end to the opposite end of said object in response to an output from said second sensor means.

12. The system of claim 11, wherein said common plenum is connected to said transportation means through a fourth valve.

13. The system of claim 12, wherein said computer control system comprises means for controlling the timing and open/closed states of said first, second, third and fourth valves and the speed of said conveyor belt.

14. The system of claim 13, wherein said control system has means to open said first valve means during a first sampling stage of said sampling period and close said second and third valves, to open said second valve means during a second sampling stage of said sampling period and close said first and third valves, to open said third valve means during a third sampling stage of said sampling period and close said first and second valves.

15. The system of claim 14, wherein said control system includes means for opening said fourth valve after the third sampling stage of said sampling period.

16. The system of claim 14, wherein said control system includes means for opening said fourth valve after each of said first, second and third sampling stages of said sampling period.

17. The system of claim 14, wherein said automated baggage/parcel sampling chamber is mobile.

18. The system of claim 14, wherein said automated baggage/parcel sampling chamber is stationary.

19. The system of claim 1, wherein said detection and screening system includes a preconcentrator for preferentially concentrating molecular vapors of said target material in said sample volume and a vapor detector. means responsive to molecular vapor from said target material.

20. The system of claim 1, wherein said detection and screening system includes means for collecting and flash vaporizing particulates containing said target materials, and a vapor detector means responsive to molecular vapors from said target materials.

21. The system of claim 1, wherein said detector and screening system collects and removes particulates from said sample value of air and converts said particulates into a vapor sample, and then separately analyzes the particulate vapor sample and any other molecular vapors present in said sample volume of air.

22. An automated baggage/parcel sampling means for obtaining sequential air samples from a plurality of baggage/parcel objects for use in a detection and screening system for detecting molecular vapor from a target material or particulates containing a target material, said target material including explosives, chemical agents, drugs or narcotics, said chamber comprising:

(a) a plurality of sampling heads containing rotating brushes for sweeping and collecting vapor from the environment surrounding the object and particulate matter attached to said object;

(b) a means for automatically moving said object through said automated baggage/parcel sampling chamber;

(c) a first sample collection and analysis subsystem for collecting target particulates contained in said sample volume of air and converting said target particulates into a first vapor sample for analysis;

(d) a second sample collection and analysis subsystem for concentrating target vapors contained in said sample volume of air, said second subsystem having first means for selectively concentrating said target vapors into a second vapor sample for analysis;

(e) detection means responsive to said target materials to generate a signal in response to the presence of said target materials in either said first or second vapor sample; and (f) a control system which controls the operation of said automated baggage/parcel sampling chamber with said sample collection and analysis subsystem.

23. An automated baggage/parcel sampling means as claimed in claim 22, wherein said first sample collection and analysis subsystem includes a particulate collector which further comprises:

(a) at least one filter element for preferentially retaining target particulates contained in said sample volume of air; and (b) a vaporization chamber adapted to receive said filter element, said vaporization chamber having means for heating said filter element to flash vaporize the retained target particulates into said first vapor sample for analysis.

24. An automated baggage/parcel sampling means as claimed in claim 23, wherein said first sample collection and analysis subsystem further comprises:

(a) first, second and third filter elements for selectively retaining target particulates contained in said sample volume air;

(b) a collection chamber for receiving said sample volume of air, said collection chamber adapted to sequentially receive one of said first, second and third filter elements to selectively enable one of said filter elements to preferentially retain said target particulates during said sampling period;

(c) a vaporization chamber adapted to receive one of said first, second and third filter elements, said vaporization chamber having a first means for heating said one of said filter elements to flash vaporize the retained target particulates into said first vapor sample for analysis; and (d) a cleaning chamber adapted to receive said one of said first, second, and third filter elements following flash vaporization, said cleaning chamber having a second means for heating said one of said filter elements to effectively vaporize any remaining particulates matter retained thereon.

25. An automated baggage/parcel sampling means as claimed in claim 22, wherein said detection and screening system includes means for collecting and flash vaporizing particulates containing said target materials, and a vapor detector means responsive to molecular vapors from said target materials.

26. A detection and screening system for baggage/parcel objects to detect target vapors or target particulates associated with a defined class of target materials such as explosives, chemical agents, drugs or narcotics that may be associated with said baggage/parcel object, said system comprising:

(a) an automated baggage/parcel sampling chamber, said chamber having a plurality of movable sampling heads for collecting vapor from the environment surrounding the object and any particulate matter attached to said object;

(b) a means for automatically moving said object through said automated baggage/parcel sampling chamber;

(c) means for collecting said target vapors or vapors emanating from said target particulates contained in said sample volume of air, at a first location;

(d) means for transporting said collected target vapors or particulate emissions to a second location;

(e) means for desorbing said target vapor or particulate emissions at said second location; and (f) detection means responsive to said target vapors or particulate emissions desorbed at said second location to generate a signal in response to the presence of said target materials in said sample volume.

27. A detection and screening system for baggage/parcel objects as claimed in claim 26, wherein said means for collecting further includes a particulate collector for collecting and vaporizing collected target particulates.

28. A detection and screening system for baggage/parcel objects as claimed in claim 27, wherein said particulate collector means comprises:

(a) at least one filter element for preferentially retaining target particulates containing said sample volume of air; and (b) a vaporization chamber adapted to receive said filter element, said vaporization chamber having means for heating said filter element to flash vaporize the retained target particulates for input into said detection means for analysis thereof.

29. A detection and screening system for baggage/parcel objects as claimed in claim 28, wherein said means for heating said filter element is a pair of electrodes which supply a heating current directly to said filter element to rapidly heat said filter element and flash vaporize said target particulates.

30. A detection and screening system for baggage/parcel objects as claimed in claim 29, wherein said means for heating said filter element vaporization chamber provides a flash heat of 250 millisecond duration which results in a rapid injection of said vaporized target particulates into said detection means.

31. A high duty cycle system for screening baggage/parcel objects to detect molecules of interest that may be in a sample value of air associated with said baggage/parcel object at rapid sampling periods, said system comprising:
   (a) a baggage/parcel sampling chamber, said chamber having a plurality of sampling heads containing rotating brushes for sweeping and collecting vapor from the environment surrounding the object and particulate matter attached to said object;
   (b) a means for automatically moving said object through said baggage/parcel sampling chamber;
   (c) a reusable filter means for reciprocal movement between a first and a second position, said reusable filter means selectively collecting particulate matter containing said molecules of interest in a collection chamber which receives said sample volume of air when said reusable filter means is in said first position;
   (d) means for flash heating said collected particulate matter in a vaporization chamber which receives said reusable filter means when said reusable filter means is in said second position, said particulates being vaporized into a stream of carrier gas to thereby entrain said molecules of interest therein;
   (e) an ion mobility spectrometer for receiving said stream of carrier gas and said entrained molecules of interest, said ion mobility spectrometer generating an output signal in response to said molecules of interest; and
   (f) control means for synchronizing said baggage/parcel sampling chamber, said means for flash heating, and a means for collecting data from said output signal.

32. A high duty cycle system for screening baggage/parcel objects as claimed in claim 31, wherein said means for collecting data first digitizes said output signal, and then averages a plurality of periodic samples.

33. A high duty cycle system for screening baggage/parcel objects as claimed in claim 32, wherein said means for collecting data averages said plurality of periodic samples after a predetermined time delay to thereby optimize the detection of said molecules of interest.

34. A high duty cycle system for screening baggage/parcel objects as claimed in claim 33, wherein said system further includes a data processing means which compares a pattern formed by said averaged periodic samples with a stored pattern, and generates an alarm condition when a match is found.

35. A high duty cycle system for screening baggage/parcel objects as claimed in claim 34, wherein said data processing means compares a pattern formed by said averaged periodic samples with a plurality of stored patterns, and generates an alarm condition when a match is found.

36. A high duty cycle system for screening baggage/parcel objects as claimed in claim 31, wherein said means for flash heating supplies an electric current to said reusable filter means to rapidly heat said filter means and flash vaporize particulates collected thereon.

37. A high duty cycle system for screening baggage/parcel objects as claimed in claim 36, wherein said means for flash heating applies heat for a duration of approximately 250 milliseconds.

38. A high duty cycle system for screening baggage/parcel objects to detect target molecules of interest that may be in a sample volume of air associated with a baggage/parcel object at a predetermined frequency, said system comprising:
   (a) a sampling chamber having a plurality of movable sampling heads collecting a sample volume of air from the environment surrounding the object and particulate matter attached to said object;
   (b) a means for automatically moving said object through said sampling chamber at said predetermined frequency;
   (c) a first sample collection and analysis subsystem operating to collect target particulates contained in said sample volume of air and convert said target particulates into a first vapor sample for analysis;
   (d) a second sample collection and analysis subsystem operating to collect and concentrate target vapors contained in said sample volume of air, and including means to selectively concentrate said target vapors into a second vapor sample for analysis;
   (e) detection means responsive to said target materials contained in said first and second vapor samples and generating respective first and second signals in response to the presence of said target molecules of interest; and
   (f) control means for synchronizing of said sampling chamber with said sample collection and analysis subsystems and enabling concurrent operation of said first and second sample collection and analysis subsystems at said predetermined frequency.

39. A high duty cycle system for screening baggage/parcel objects as claimed in claim 37 wherein said first sample collection and analysis subsystem includes a particulate collector which further comprises:
   (a) at least one filter element for preferentially retaining target particulates contained in said sample volume of air; and
   (b) a vaporization chamber adapted to receive said filter element, said vaporization chamber having means for heating said filter element to flash vaporize the retained target particulates into said first vapor sample for analysis.

40. A high duty cycle system for screening baggage/parcel objects as claimed in claim 39 wherein said first sample collection and analysis subsystem further comprises:
   (a) first, second and third filter elements for selectively retaining target particulates contained in said sample volume air;
   (b) a collection chamber for receiving said sample volume of air, said collection chamber adapted to sequentially receive one of said first, second and third filter elements to selectively enable one of said filter elements to preferentially retain said target particulates during said sampling period;
   (c) a vaporization chamber adapted to receive one of said first, second and third filter elements, said vaporization chamber having a first means for heating said one of said filter elements to flash vaporize the retained target particulates into said first vapor sample for analysis; and
   (d) a cleaning chamber adapted to receive said one of said first, second, and third filter elements following flash vaporization, said cleaning chamber having a second means for heating said one of said filter elements to effectively vaporize any remaining particulates matter retained thereon.

41. A high duty cycle system for screening baggage/parcel objects as claimed in claim 38 wherein said detection and screening system includes means for collecting and flash vaporizing particulates containing said target materials, and a vapor detector means responsive to molecular vapors from said target materials.

42. A high duty cycle system for screening baggage/parcel objects as claimed in claim 38 wherein said first sample and analysis subsystem includes a means for preferentially collecting and flash vaporizing said target particulates into said first vapor sample for analysis.

43. A high duty cycle system for screening baggage/parcel objects as claimed in claim 42 wherein said first sample and analysis subsystem further includes a first gas supply means to provide a gas flow during flash vaporization to sweep molecular vapor from said vaporized particulates into said detection means.

44. A high duty cycle system for screening baggage/parcel objects as claimed in claim 43 wherein means for preferentially collecting and flash vaporizing said target particulates applies heat to said particulates for approximately 250 milliseconds.

* * * * *

UNITED STATES PATENT AND TRADEMARK OFFICE
CERTIFICATE OF CORRECTION

PATENT NO. : 5,585,575
DATED : December 17, 1996
INVENTOR(S) : Colin Corrigan, et al.

It is certified that error appears in the above-identified patent and that said Letters Patent is hereby corrected as shown below:

On the Title Page, Section [56], under "U.S. PATENT DOCUMENT", line 1: "Lerner" should read --Lerner et al.--

Column 4, line 61: "over-all" should read --over all--
Column 5, line 67: "nigh" should read --high--
Column 9, line 33: "election" should read --electron--
Column 14, line 6: "16" should read --216--
Column 15, line 2: after "discussed" delete --.--
Column 15, lines 57 & 63: "cheer" should read --chamber--
Column 16, line 26: "cheer" should read --chamber--
Column 18, line 18: "The-first" should read --The first--
Column 20, line 25: "by-the' should read --by the--
Column 20, line 56: "to-thereby" should read --to thereby--
Column 23, line 19: "41B" should read --418--
Column 24, lines 43 & 47: "cheer" should read --chamber--
Column 31, line 37: "tagent" should read --agent--
Column 31, line 61: "trinitiaramine" should read --trinitrotoluene--
Column 32, line 17: "by" should read --be--
Column 36, line 23: "are-developed" should read --are developed--
Column 38, line 43: after "parcel" delete --.--
Column 40, line 66, Claim 19: after "detector" delete --.--
Column 41, line 8, Claim 21: "value" should read --volume--

UNITED STATES PATENT AND TRADEMARK OFFICE
CERTIFICATE OF CORRECTION

PATENT NO. : 5,585,575
DATED : December 17, 1996
INVENTOR(S) : Colin Corrigan, e.t al.

It is certified that error appears in the above-identified patent and that said Letters Patent is hereby corrected as shown below:

Column 43, line 3, Claim 31: "value" should read --volume--.

Signed and Sealed this

Second Day of June, 1998

Attest:

BRUCE LEHMAN

*Attesting Officer*  Commissioner of Patents and Trademarks